United States Patent
Li et al.

(10) Patent No.: US 11,014,088 B2
(45) Date of Patent: May 25, 2021

(54) SENSITIVE ELISA FOR DISEASE DIAGNOSIS ON SURFACE MODIFIED POLY(METHYL METHACRYLATE) (PMMA) MICROFLUIDIC MICROPLATES

(71) Applicants: Xiujun Li, El Paso, TX (US); Sanjay S. Timilsina, El Paso, TX (US)

(72) Inventors: Xiujun Li, El Paso, TX (US); Sanjay S. Timilsina, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 138 days.

(21) Appl. No.: 15/454,200

(22) Filed: Mar. 9, 2017

(65) Prior Publication Data

US 2017/0261504 A1    Sep. 14, 2017

Related U.S. Application Data

(60) Provisional application No. 62/305,622, filed on Mar. 9, 2016.

(51) Int. Cl.
*B01L 3/00* (2006.01)
*G01N 33/543* (2006.01)

(52) U.S. Cl.
CPC ...... *B01L 3/5085* (2013.01); *G01N 33/54353* (2013.01); *G01N 33/54366* (2013.01); *B01L 2300/0829* (2013.01); *B01L 2300/0858* (2013.01)

(58) Field of Classification Search
CPC ........... B01L 3/5085; B01L 2300/0858; B01L 2300/0829; G01N 33/54366; G01N 33/54353
See application file for complete search history.

(56) References Cited

U.S. PATENT DOCUMENTS

| | | | |
|---|---|---|---|
| 4,444,487 A | 4/1984 | Miller et al. | 399/337 |
| 4,745,055 A | 5/1988 | Schenk et al. | 435/7.6 |
| 5,702,906 A * | 12/1997 | Rosenthal | 435/7.1 |
| 6,528,264 B1 * | 3/2003 | Pal | B82Y 30/00 506/32 |
| 2003/0219713 A1 * | 11/2003 | Valencia | 435/4 |
| 2004/0241675 A1 * | 12/2004 | Gillner | B01J 19/0046 435/6.11 |
| 2004/0260019 A1 * | 12/2004 | Kaplan | C07K 1/1077 506/30 |
| 2006/0081835 A1 * | 4/2006 | Hutchison | H01L 51/0595 257/17 |
| 2006/0099704 A1 * | 5/2006 | Predki | G01N 33/6842 705/301 |
| 2007/0264676 A1 * | 11/2007 | Yang | 435/7.92 |
| 2010/0130380 A1 * | 5/2010 | Nokihara | B01L 3/5085 506/13 |
| 2010/0184622 A1 * | 7/2010 | Nokihara | B01J 19/0046 506/15 |
| 2010/0248977 A1 * | 9/2010 | Johnston | C07K 7/08 506/9 |
| 2013/0210035 A1 * | 8/2013 | Wu | G01N 33/723 435/7.92 |
| 2015/0166978 A1 * | 6/2015 | Cooney | C12N 11/14 422/44 |

FOREIGN PATENT DOCUMENTS

| | | |
|---|---|---|
| EP | 120694 | 10/1984 |
| EP | 125023 | 11/1984 |
| EP | 256654 | 2/1988 |
| WO | WO/88/03565 | 5/1988 |

OTHER PUBLICATIONS

Bai et al. "Enzyme-linked immunosorbent assay of *Escherichia coli* O157:H7 in surface enhanced poly(methyl methacrylate) microchannels." *Biotechnol Bioeng*. 2007, 98(2):328-339.
Bai et al. "Surface modification for enhancing antibody binding on polymer-based microfluidic device for enzyme-linked immunosorbent assay." *Langmuir*. 2006, 22(22):9458-9467.
Brown et al. "Fabrication and characterization of poly(methylmethacrylate) microfluidic devices bonded using surface modifications and solvents." *Lab Chip*. 2006, 6(1):66-73.
Bulmus et al., "Modified PMMA monosize microbeads for glucose oxidase immobilization," *Chemical Engineering Journal*, 1997, 65:71-76.
Dodge et al., "Electrokinetically driven microfluidic chips with surface-modified chambers for heterogeneous immunoassays." *Analytical chemistry*, 2001, 73:3400-3409.
Falkner et al., "Expression of mouse immunoglobulin genes in monkey cells." *Nature* 298:286, 1982.
Fauci et al., "The perpetual challenge of infectious diseases." *New England Journal of Medicine*, 2012, 366:454-461.
Ganem et al., "Hepatitis B virus infection—natural history and clinical consequences." *New England Journal of Medicine*, 2004, 350:1118-1129.

(Continued)

*Primary Examiner* — Ann Y Lam
(74) *Attorney, Agent, or Firm* — Norton Rose Fulbright US LLP

(57) ABSTRACT

Certain embodiments are directed to an ultrasensitive poly (methyl methacrylate) (PMMA) ELISA microfluidic microplate, where the protein is covalently bound to a poly-lysine modified or carboxylated PMMA surface.

18 Claims, 19 Drawing Sheets

(56) References Cited

OTHER PUBLICATIONS

Henry et al., "Surface modification of poly(methyl methacrylate) used in the fabrication of microanalytical devices." *Analytical chemistry*, 2000, 72:5331-5337.
Herrmann, "Enzymatically-generated fluorescent detection in microchannels with internal magnetic mixing for the development of parallel microfluidic ELISA." *Lab on a Chip*, 6, 2006, 555-560.
Jaroszewicz et al., "Hepatitis B surface antigen (HBsAg) levels in the natural history of hepatitis B virus (HBV)-infection: a European perspective." *Journal of hepatology*, 2010, 52:514-522.
Lai et al., "Viral hepatitis B." *The Lancet*, 2003, 362:2089-2094.
Llopis et al. "Surface modification of poly(methyl methacrylate) microfluidic devices for high-resolution separations of single-stranded DNA." *Electrophoresis*. 2007, 28(6):984-993.
Mao et al., "Design and characterization of immobilized enzymes in microfluidic systems." *Analytical chemistry*, 2002, 74:379-385.
Morrison et al., "Transfer and expression of immunoglobulin genes." *Ann Rev. Immunol* 2, pp. 239-256, 1984.
Morrison, "Sequentially derived mutants of the constant region of the heavy chain of murine immunoglobulins." *J. Immunol*. 123:793-800, 1979.
Ren et al., "Bioactive gelatin-siloxane hybrids as tissue engineering scaffold," *Solid State Phenomena*, 2006, 111:13-18.
Rodella et al., "Quantitative analysis of HBsAg, IgM anti-HBc and anti-HBc avidity in acute and chronic hepatitis B." *Journal of clinical virology*, 2006, 37:206-212.
Sato et al. "Determination of carcinoembryonic antigen in human sera by integrated bead-bed immunoassay in a microchip for cancer diagnosis." *Analytical Chemistry*, 2001, 73:1213-1218.
Tabata et al., "Protein release from gelatin matrices." *Advanced drug delivery reviews*, 1998, 31:287-301.
Toepke et al., "PDMS absorption of small molecules and consequences in microfluidic applications." *Lab Chip*, 2006, 6:1484-1486.

* cited by examiner

SENSITIVE ELISA FOR DISEASE DIAGNOSIS ON SURFACE MODIFIED POLY(METHYL METHACRYLATE) (PMMA) MICROFLUIDIC MICROPLATES

PRIORITY CLAIM

This application claims priority to U.S. Application No. 62/305,622 filed Mar. 9, 2016, which is incorporated herein by reference in its entirety.

BACKGROUND

There is a fragile balance with respect to continual emergence of new infectious disease and the reemergence of old infectious disease, together with the potential for their global spread (Nelson and Williams, *Infectious disease epidemiology,* Jones & Bartlett Publishers, 2014). Infectious disease stand out among many challenges to health because of their profound impact on human species, unpredictable and explosive global effects due to their pandemics. Unlike other diseases, which can result from multiple interacting risk factors, most infectious disease are caused by single agent, the identification of which leads not only the control measures but treatment measures as well (Fauci and Morens, *New England Journal of Medicine,* 2012, 366:454-461). This underlines the need of accurate surveillance and the development of new strategies for fast, rapid, and sensitive detection of infectious diseases for their control.

Enzyme Linked ImmunoSorbent Assay (ELISA) is one of the most commonly and widely used laboratory methods in medical diagnostic, food industry (food allergen), plant pathology, quality control, toxicology, and research applications. ELISA utilizes antibodies and color change to identify a substance. This biochemical assay detects proteins both quantitatively and qualitatively based on their binding to immobilized antibodies or antigens. Most ELISAs are performed in 96-well plates and take several hours to complete because of the hour-long incubation and blocking time, as well as consume large volumes of precious samples and reagents, and must be performed in lab, which is not suitable for point-of-care detection. Highly complicated and specialized instruments have been developed to automate the assay, including robotic pipetters, plate washers, and optical colorimetric detectors.

The sensitivity of the bioassay performed on a microfluidic device depends upon the total activity of the proteins or enzymes attached to the surface of the microfluidics chip. The interaction of the protein with the chip surface has a profound effect on sensitivity and specificity of the immunoassay. The hydrophobic physical adsorption of proteins onto the microfluidics surface may reduce functional site or activity of protein by even more then 90% (Ren et al. *Solid State Phenomena,* 2006, 111:13-18; Tabata and Ikada, *Advanced drug delivery reviews,* 1998, 31:287-301) and may result in strong non-specific binding (Toepke and Beebe, *Lab Chip,* 2006, 6:1484-1486). So, to increase the sensitivity and binding efficiency of the microfluidic chip, an appropriate surface modification is required. Many different kinds of binding between protein and the polymer surface has been defined; passive adsorption on polymer beads (Sato et al. *Analytical Chemistry,* 2001, 73:1213-18), lipid layer grafted on PDMS (Mao et al., *Analytical chemistry,* 2002, 74:379-85), and protein A bound to PDMS surface (Dodge et al., *Analytical chemistry,* 2001, 73:3400-09).

Functionalization of PMMA with amine groups have been reported but consists of too many steps and yielded a low amine density (Bulmu et al., *Chemical Engineering Journal,* 1997, 65:71-76) or involves unstable intermediates and non-environment friendly solvents (Henry et al., *Analytical chemistry,* 2000, 72:5331-37).

Brown et al. (*Lab Chip.* 2006, 6(1):66-73) characterized the surface modification of PMMA microfluidic devices. PMMA surfaces, which were modified using air plasma, acid catalyzed hydrolysis, and aminolysis (using ethylenediamine), to determine if covalent and or hydrogen bonds between modified PMMA substrate and cover plate increase the adhesion. Llopis et al. (*Electrophoresis.* 2007, 28(6): 984-93) studied the surface modification of PMMA microfluidic devices for high-resolution separation of single-stranded DNA. They created an amine terminated PMMA surface by chemical or photochemical process by using ethylenediamine, which was then used to covalently anchor methacrylic acid used as scaffold to produce linear polyacrylamides (LPAs). It helped them increase the efficiency of separation of single stranded DNA electrophoretically. Bai et al. (*Langmuir.* 2006, 22(22):9458-67) studied the surface modification of PMMA to enhance the antibody binding on polymer-based microfluidic device to perform ELISA. They found that the poly(ethyleneimine) modified PMMA was 10 times more active in binding antibodies as compared to those without treatment or treated with small amine-bearing molecule, hexamethylenediamine (HMD). They performed the ELISA of IgG with a similar detection limit as the conventional 96-well plate microtiter plate. Bai et al. (*Biotechnol Bioeng.* 2007, 98(2):328-39) performed ELISA of *Escherichia coli* on PEI modified PMMA.

SUMMARY

Unspecific absorption of protein often leads to high background and low sensitivity in enzyme linked immunosorbent assay (ELISA). Covalent binding of proteins can enhance the binding efficiency and improve the immunoassay sensitivity. Herein, the inventors have developed a simple, miniaturized poly(methyl methacrylate) (PMMA) ELISA microfluidic microplate, where the protein is covalently bound to poly-lysine modified or carboxylated PMMA surface. The modification with poly-lysine can be used to aminate the PMMA surface. In certain aspects the carboxylated PMMA surface is further modified to an amine-reactive sulfo-NHS ester. In certain aspects the modified surface of PMMA is used for covalently coupling peptides or polypeptide to the PMMA surface. Unlike ELISA in traditional microplates, which is often limited by long incubation and blocking time—rapid and ultrasensitive detection of disease biomarkers can be completed within 90 min in this microplate with much less reagent consumption. Immunoassays do not require expensive and sophisticated equipment and results can even be observed by the naked eye. Quantitative analysis can be achieved by calculating the brightness of images scanned by a desktop scanner. Although no specialized ELISA equipment was used, the limits of detection of 200 pg/mL for Immunoglobulin G (IgG), 180 pg/mL for Hepatitis B surface antigen (HBsAg), and 300 pg/mL for Hepatitis B core antigen (HBcAg) have been achieved using a poly-lysine modified PMMA microplate, which are at least 10 fold more sensitive as compared to commercial ELISA kits. In addition, limits of detection of 190 pg/mL for IgG, 360 pg/mL for HBsAg, and 380 pg/mL for HBcAg have been achieved using carboxylated PMMA surface which are also at least 10 fold more sensitive as compared to commercial ELISA kits.

In certain aspects the microplate can comprise 8, 96, 192, 384, 800 or more microwells or chambers, including all values and ranges there between. A microwell can be 0.001, 0.01, 0.1, 0.5, 1, 2, or 3 mm in diameter, including all values there between and 0.01, 0.1, 1, 2, 3, or 4 mm in depth, including all values there between. In a further aspect, the microwells can be arranged in an array. In certain aspects the array is, but need not be, a regular array such as a linear or radial array. In certain aspects the microwell array can be arranged in a 1, 2, 4, 6, 8, 10, 12 or more rows by 1, 2, 4, 6, 8, 10, 12, 24 or more columns. In a further aspect the array can be arranged in 2, 4, 5, 8, 10, 12 or more radii. A horizontal cross section of the microwell can form any geometric shape, such as a circular, square, rectangle, triangle, etc. In certain aspects the microwell has a circular horizontal cross section. In certain aspects the microwell can have a flat or rounded floor. In certain aspects the detection well is a funnel shaped well, with different upper well diameters (e.g. about 0.01, 0.1, 1, 2, 3, 4, or 5 mm, including all values and ranges there between) and lower well diameters (e.g. 0.01, 0.1, 0.2, 0.3, 0.4, 0.5, to 1 mm, including all values and ranges there between). In certain aspects the lower well diameters are smaller than upper well diameters.

Certain embodiments are directed to methods of detecting an analyte(s) comprising introducing a sample suspected of having or comprising a target analyte(s) into a device described herein. Subjecting the sample to detection or manipulation and detection, wherein if a target is present in the sample an analyte binds to a probe and produces a detectable signal. In certain aspects the device is configured to detect a plurality of targets at once (multiplexed assay) with a separate and distinct probe in an individual detection microwell, or separate and distinguishable probes in the same microwell.

The term "analyte" or "target analyte" refers to a compound or composition to be detected or measured in the test sample. The analyte will bind a probe, aptamer, or other capture agent. In certain aspects the capture agent is covalently attached to a surface. An analyte can be an antigenic substance, hapten, antibody and combination thereof. The analyte of interest in an assay can be, for example, a protein, a peptide, an amino acid, a nucleic acid, a hormone, a steroid, a vitamin, a pathogenic microorganism, a natural or synthetic chemical substance, a contaminant, a drug, or metabolite.

The term "probe" or "capture agent" refers to a molecule that can detectably distinguish between target molecules differing in structure. Detection can be accomplished based on identification of specific binding with a target. Examples of such specific binding include peptides, proteins, antibodies, antibody fragments, or other affinity reagents.

The term "antibody" as used herein includes immunoglobulin molecules and immunologically active portions of immunoglobulin molecules, i.e., molecules that contain an antigen-binding site that specifically binds (immunoreacts with) an antigen. The term "antibody" as used herein also includes antibody-like molecules, such as aptamers. A naturally occurring antibody (e.g., IgG, IgM, IgD) includes four polypeptide chains, two heavy (H) chains and two light (L) chains interconnected by disulfide bonds. However, it has been shown that, fragments of a naturally occurring antibody can perform the antigen-binding function of an antibody. Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an FIT fragment consisting of the $V_L$ and $V_H$ domains of a single arm of an antibody, (iv) a dAb fragment (Ward et al., Nature 341:544-546, 1989); and (vi) a F(ab')$_2$ fragment. Immunoglobulins and certain variants thereof are known and many have been prepared in recombinant cell culture (e.g., see U.S. Pat. Nos. 4,745,055 and 4,444,487; WO 88/03565; EP 256,654; EP 120,694; EP 125,023; Falkner et al., Nature 298:286, 1982; Morrison, J. Immunol. 123:793, 1979; Morrison et al., Ann Rev. Immunol 2:239, 1984).

The phrase "specifically binds" to a target refers to a binding reaction that is determinative of the presence of the target in the presence of a heterogeneous population of other biologics. Thus, under designated conditions, a specified molecule binds preferentially to a particular target and does not bind in a significant amount to other biologics present in the sample.

As used herein, the term "sample" or "test sample" generally refers to a material suspected of containing one or more targets. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. The test sample may be pretreated prior to use, such as preparing plasma from blood, diluting viscous fluids, lysing microbes in the sample, and the like. Methods of treatment may involve filtration, precipitation, dilution, distillation, mixing, concentration, inactivation of interfering components, lysing organisms and/or cells, and the addition of reagents. Besides physiological fluids, other liquid samples may be used such as water, food products, and the like for the performance of environmental or food production assays. In addition, a solid material suspected of containing the target may be used as the test sample. In some instances it may be beneficial to modify a solid test sample to form a liquid medium or to release a target (e.g., a nucleic acid).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
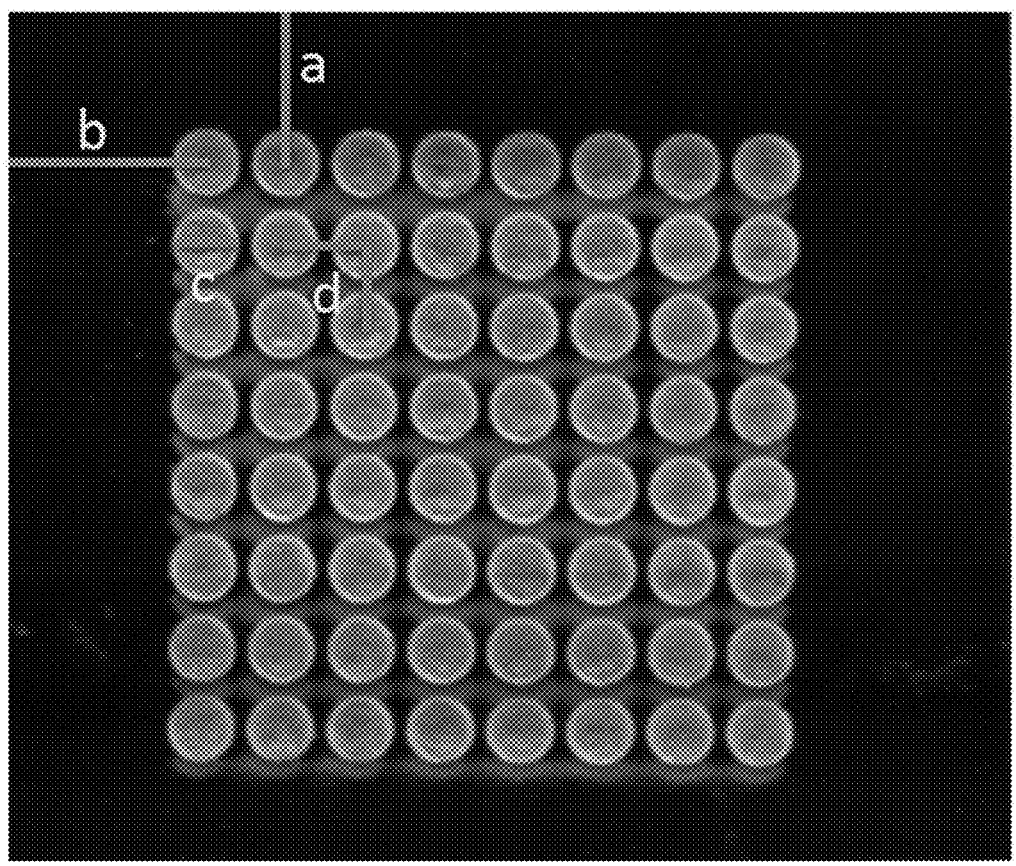
FIG. 1. Photograph of the actual device with black background.

Infectious diseases, cancer, and other diseases are often diagnosed by immunoassay. Enzyme Linked ImmunoSorbent Assay (ELISA), one of the most commonly and widely used laboratory immunoassay methods in medical diagnostic and research applications, detects proteins based on their binding to immobilized antibodies or antigens. Even though, most ELISAs today are performed in 96-well plates and are well suited for high-throughput assays, highly complicated and specialized instruments have to be utilized to automate the assay, including robotic pipetters, plate washers, and spectrophotometers. These traditional quantitative immunoassay experiments take several hours to complete because of the hour-long incubation. Likewise, other critical issue is the consumption of large volumes of precious samples and reagents, and must be performed in a laboratory setting, which is not suitable for point-of-care detection. The progress in the field of microfluidics and MEMS technology could provide an ELISA system for real time detection, multiplexing, and reducing sample usage, for economical and high throughput diagnosis (Herrmann, (2006) *Lab on a Chip*, 6, 555-560).

In certain aspects a microtiter plate is made from poly (methyl methacrylate) (PMMA). PMMA has various advantages over other expensive substrates. It is more rigid and less fragile, disposable, and easy to fabricate using techniques such as hot embossing or $CO_2$ laser ablation. Also, it does not require the longer fabrication and incubation time required for PDMS. In certain aspects PMMA is modified with polylysine or carboxylation so there is covalent binding of protein to the PMMA surface, increasing its specificity and sensitivity. Certain aspects are directed to multiplex detection of different biomarkers, for example Hepatitis B (Hepatitis B Surface antigen (HBsAg) and Hepatitis B core Antigen (HBcAg)). A microfluidics chip is created for sensitive and specific multiplex disease detection using modified PMMA, which can be both used in remote setting without laboratory facility, and also in developed countries with sophisticated instruments like microplate reader.

Hepatitis B virus (HBV) is used as a representative disease/biomarker for proof of concept studies. HBV infection is a major cause of chronic hepatic damage and of hepatocellular carcinomas worldwide (Lai et al., *The Lancet*, 2003, 362:2089-94). HBsAg, a qualitative serological biomarker for a developing HBV infection, can diagnose acute and chronic hepatitis B virus (Rodella et al., *Journal of clinical virology*, 2006, 37:206-12; Jaroszewicz et al., *Journal of hepatology*, 2010, 52:514-22; Ben Slama et al., *Gastroentérologie Clinique et Biologique*, 2010, 34:S112-S118). Also, the titer of serum HBsAg indicates the level of infection and severity of disease (Ben Slama et al., *Gastroentérologie Clinique et Biologique*, 2010, 34:S112-S118; Ganem and Prince, *New England Journal of Medicine*, 2004, 350:1118-29).

In one embodiment a microfluidic chip is prepared from poly-lysine modified or carboxylated PMMA, which is a less expensive replacement of microplate that can be used to read data by microtiter plate or scanner for low resource setting. It is economical; does not require trained personnel or considerable volumes of biological samples. Similarly, all the reagent delivery and washing steps can be integrated into the device so that it does not require robust method of reagent delivery into each well manually. In one aspect a funnel shaped PMMA has been created by laser ablation of PMMA. In certain embodiments the ELISA takes place on the upper surface of funnel, which is poly-lysine modified or carboxylated.

Certain aspects of the invention are directed to immunoassays, immunoassay devices, and immunoassay kits for detecting one or more target analyte. Immunoassays generally involve contacting with a sample directly or indirectly with a capture agent. In certain aspects the capture agent can be a polypeptide. In other aspects the capture agent can be directly or indirectly linked to a solid support, i.e., modified PMMA as described herein. Specific binding of a capture agent with a target analyte from the sample can then be detected. In certain aspects the capture agent is an antibody and the antibody can be detected by an antibody detecting polypeptide, e.g., a secondary antibody. In certain aspects the capture agent is covalently linked to the solid support, i.e., the poly-lysine modified or carboxylated PMMA microtiter plate described herein.

In a particular aspect, an immunoassay may be carried in one or more of the following steps: (i) a poly-lysine modified or carboxylated PMMA support is coated with a capture polypeptide or agent (e.g., an antibody), (ii) the support is washed and then blocked with a blocking buffer, (iii) the support is washed and a detection reagent (e.g., a secondary antibody) is added, (iv) the support can be washed and the appropriate detection reagents or methodology added or performed; and (v) the support is examined or assessed for any detectable signal.

In certain aspects a label is capable of generating a measurable signal when it is contacted with the appropriate substrate or stimulus (e.g., light comprising an appropriate wavelength of electromagnetic radiation). In some embodiments, the detection reagent is conjugated to a label selected from horseradish peroxidase (HRP), $I^{125}$, alkaline phosphatase, fluorescein isothiocyanate (FITC), tetramethyl rhodamine isothiocyanate (TRITC), green fluorescent protein (GFP), allophycocyanin, phycocyanin, phycoerythrin, and phycoerythrocyanin. In some embodiments, the detection reagent is not labeled, and can be detected, for example, with a secondary antibody, that is optionally labeled.

Other embodiments are directed to an assay kit comprising a poly-lysine modified or carboxylated PMMA support. In one particular aspect, the kit may contain an antibody capture polypeptide, a capture antibody, and/or an antibody detection polypeptide. The kits of the invention may further contain at least one of following reagents for carrying out the immunoassay such as blocking buffer, stopping reagents, a label substrate, and washing solutions, for example.

According to other embodiments, an assay device used for detecting target analytes may include a poly-lysine modified or carboxylated PMMA support coated with 1, 2, 3, 4, 5, 6, 7, 8, 9, 10 or more capture agents (e.g., capture polypeptide or an antibody). The immunoassay device of the invention may include a capture agent linked to the poly-lysine modified or carboxylated PMMA substrate.

In certain aspects the poly-lysine modified or carboxylated PMMA substrate can be part of a microfluidic chip. For example, the chip used in this study was designed in Adobe Illustrator CS5 and micro-machined using Laser cutter (Epilog Zing 16, Golden, Colo.). In certain aspects the wells in the PMMA layer are designed according to the dimension of standard 384 well plate. In one example, as seen from FIG. 1, the X-axis and Y-axis offset is 4.5 mm (d), which, is the length between the centers of 2 wells. The position of the first well corresponds to A1 of microtiter plate, with the center of first well. A1 row offset of the chip is 8.99 mm (a), similar to microtiter plate. In addition, A1 column offset of 12.13 mm (b) is same as microtiter plate. The diameter of each well is 3.6 mm.

Covalent Modification of PMMA

Figure 2A:
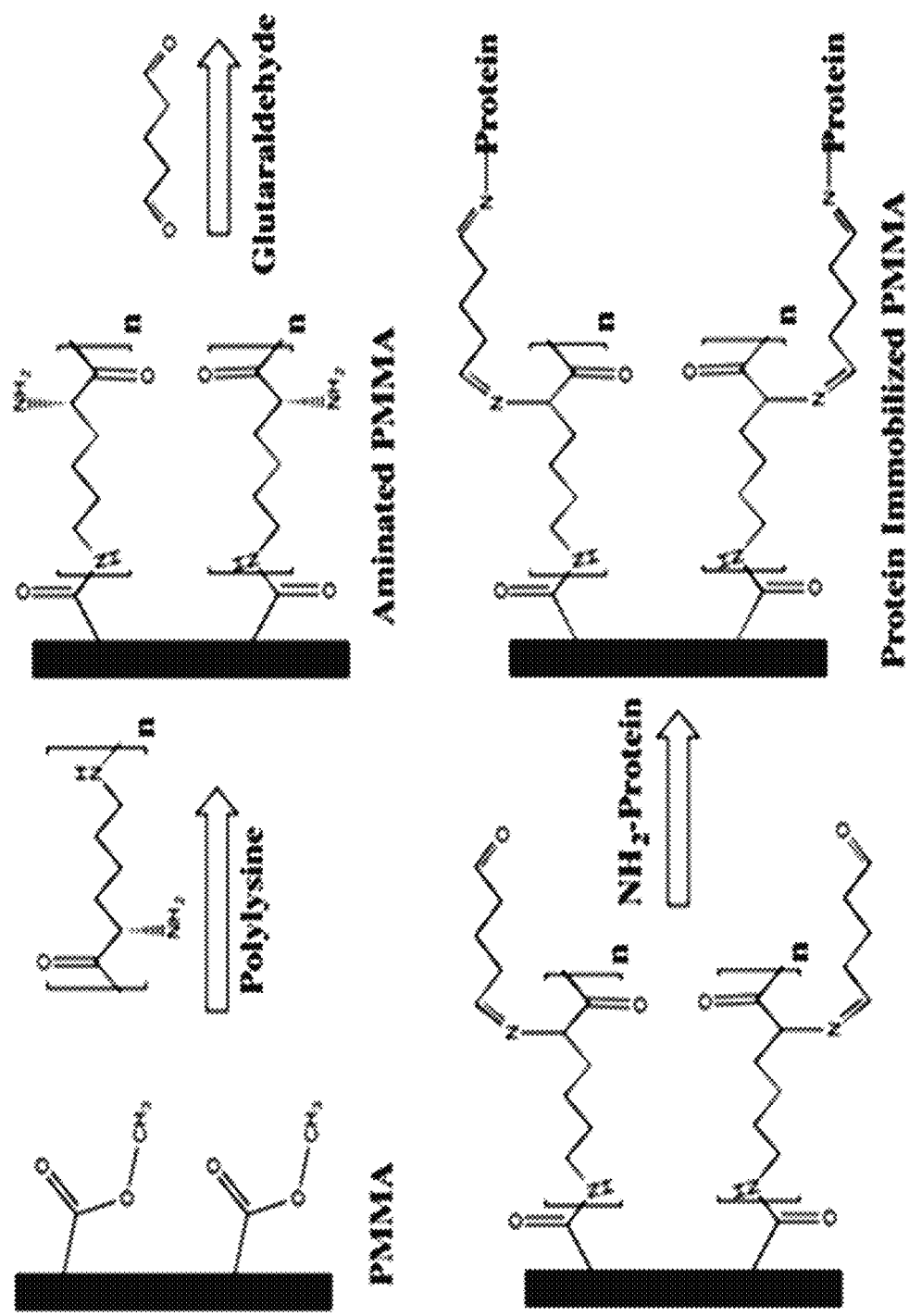
FIG. 2A-2B. Schematic of the covalent modification of PMMA. A. poly-lysine modification; B. Carboxylation.

FIG. 2A illustrates one method for covalent modification of PMMA. First PMMA is sonicated for 10 minutes in 50% aqueous 2-propanol solution. PMMA is dried. After drying the dried PMMA is immersed in poly-lysine (e.g., 0.2%, 0.1%, or 0.05% poly-lysine solutions) in DMSO for 20 minutes at room temperature. PMMA is then rinsed with 2-Propanol. Finally, PMMA is immersed in Glutaraldehyde solution (1% w/v) at room temperature for 30 minutes. Once the PMMA is poly-lysine modified a protein is added so that there is covalent binding of protein to the PMMA surface.

In an alternatively method, PMMA is immersed in 1N NaOH solution at 55° C. for 30 minutes. Then PMMA is immerged in a poly-lysine solution (e.g., 0.2%, 0.1%, or 0.05%) at pH 7 at room temperature for 1 hour. Finally, PMMA is immersed in Glutaraldehyde solution (1% w/v) at room temperature for 30 minutes. Once the PMMA is poly-lysine modified, protein is added so that there is covalent binding of protein to the PMMA surface.

Figure 2B:
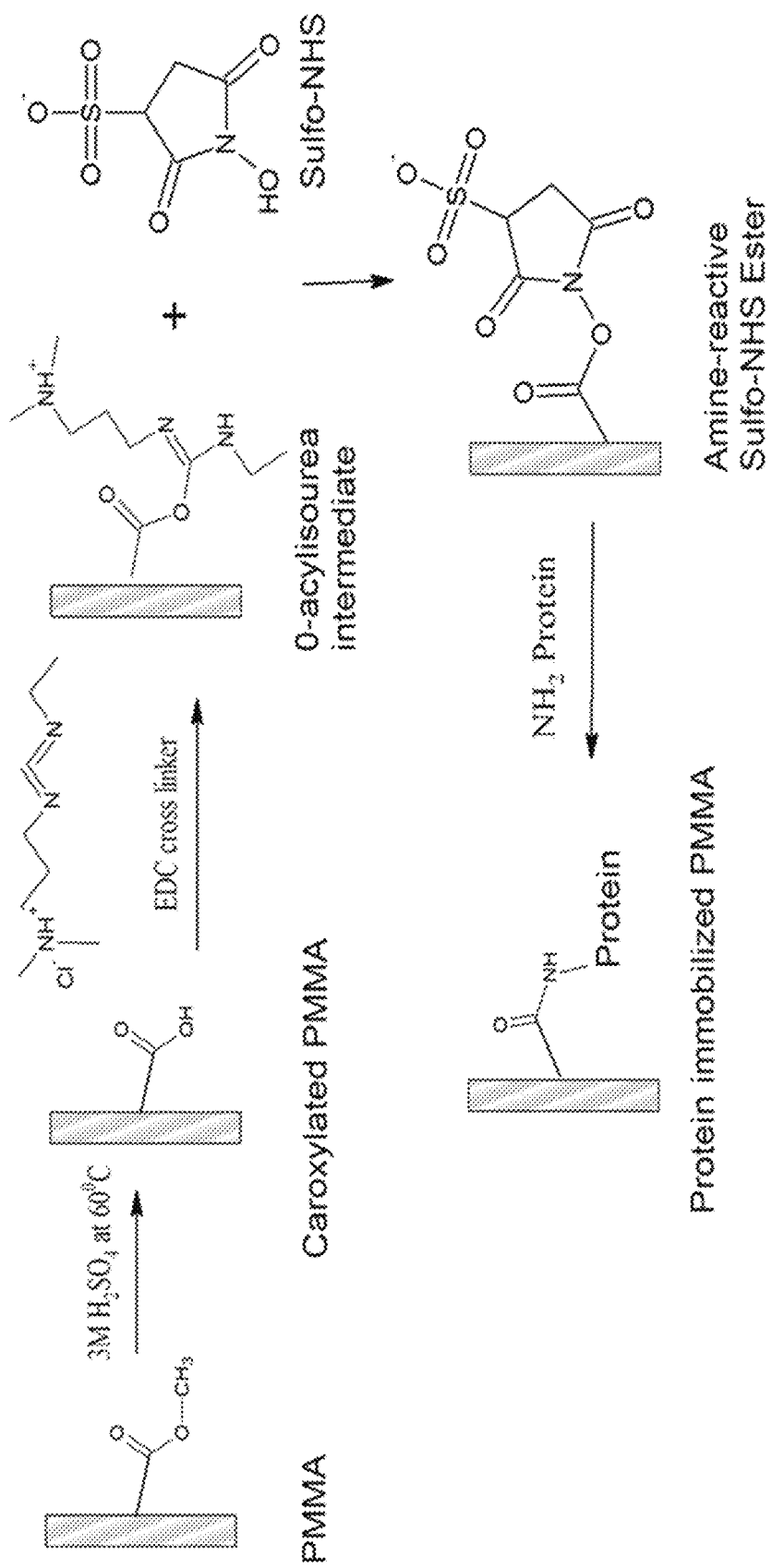

In yet another method of modification PMMA can be carboxylated (see FIG. 2B). Carboxylation methods include sonication of PMMA for 10 minutes in 50% aqueous 2-propanol solution. PMMA is dried. PMMA is then submerged in 3M sulfuric acid at 60 degrees for 20 minutes. After that it is rinsed first with water, then with 2-propanol and dried. Then EDC/NHS solution (0.35M EDC+0.1M NHS) is added and incubated for 15-20 minutes. Once the PMMA is modified, protein is added so that there is covalent binding of protein to the PMMA surface.

FTIR Analysis of Modified PMMA Surface

From FT-IR spectrum of the poly-lysine modified PMMA, it can be seen that there is a distinct absorption band from 1,150 $cm^{-1}$ to 1,250 $cm^{-1}$, which can be attributed to the C—O—C stretching vibration. The two bands at 1,387 $cm^{-1}$ and 750 $cm^{-1}$ can be attributed to the α-methyl group vibrations. The band at 986 $cm^{-1}$ is the characteristic absorption vibration of PMMA, together with the bands at 1,063 $cm^{-1}$ and 841 $cm^{-1}$. The band at 1,723 $cm^{-1}$ shows the presence of the acrylate carboxyl group. The band at 1,435 $cm^{-1}$ can be attributed to the bending vibration of the C—H bonds of the —$CH_3$ group. The two bands at 2,995 $cm^{-1}$ and 2,951 $cm^{-1}$ can be assigned to the C—H bond stretching vibrations of the —$CH_3$ and —$CH_2$— groups, respectively.

Figure 3A:
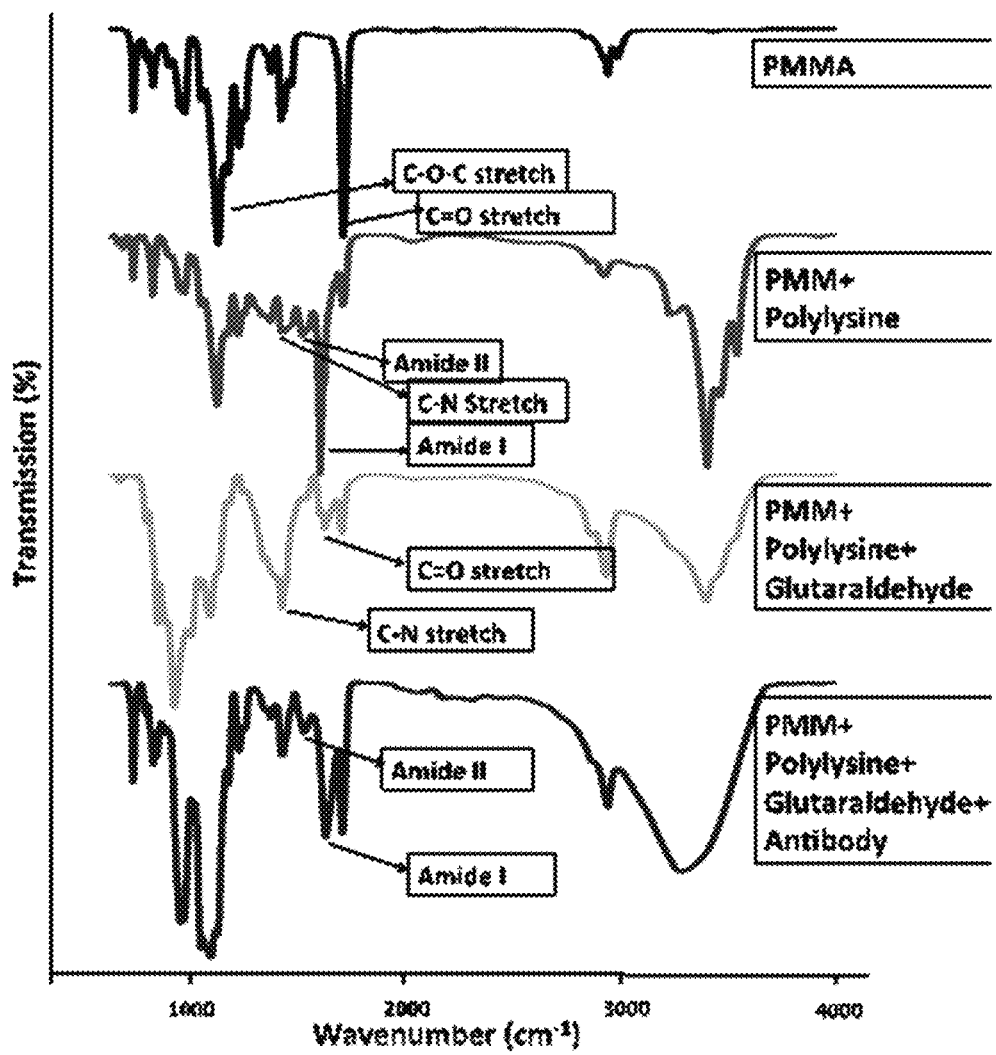
FIG. 3A-3C. FTIR analysis of surface modified PMMA. A. poly-lysine modification, method 1 (poly-lysine in Dimethyl sulfoxide (DMSO)); B. poly-lysine modification, method 2 (poly-lysine in Sodium hydroxide (NaOH) treated PMMA); C. Carboxylation.

Poly-lysine modification method 1 (FIG. 3A). Some major changes can be observed in the spectrum of PMMA once it was modified. The presence of Amide I (1652 $cm^{-1}$), Amide II (1533 $cm^{-1}$) and C—N stretch after the treatment of PMMA with polylysine shows that the PMMA is aminated by Polylysine. The aminated PMMA was further treated with glutaraldehyde as can be seen from C=O (1637 $cm^{-1}$) and C—N (1442 $cm^{-1}$) stretch vibration to covalently bind the antibody to the PMMA surface. The inventors see strong absorption for Amide I (1646 $cm^{-1}$) and Amide II (1555 $cm^{-1}$) after the addition of an antibody, which proves the covalent binding of the antibody to the modified PMMA surface.

Figure 3B:
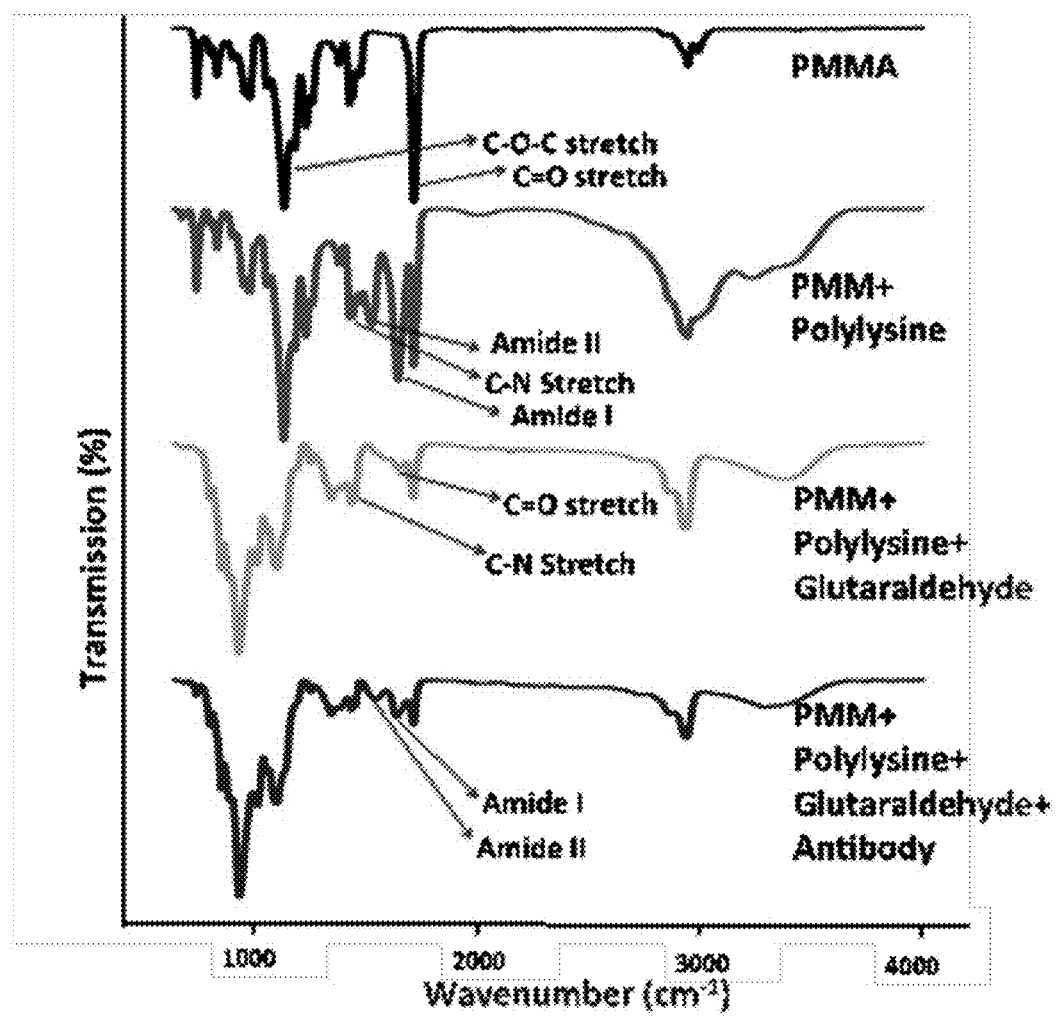

Poly-lysine modification method 2 (FIG. 3B). Some major changes can be observed in the spectrum of PMMA once it was treated with NaOH to get hydroxyl group followed by treatment with polylysine to get aminated PMMA. The presence of Amide I (1617 $cm^{-1}$), Amide II (1534 $cm^{-1}$) and C—N (1435 $cm^{-1}$) stretch after the treatment of PMMA with polylysine shows that the PMMA is aminated by Polylysine. Also, we can see $CH_2$ stretching mode of vibration at 2933 $cm^{-1}$ and V1 proton mode band of peptide at 3239 $cm^{-1}$. The aminated PMMA was further treated with glutaraldehyde as can be seen from C=O (1637 $cm^{-1}$) and C—N (1440 $cm^{-1}$) stretch vibration to covalently bind the antibody to the PMMA surface. The inventors can see strong absorption for Amide I (1643 $cm^{-1}$) and Amide II (1541 $cm^{-1}$) after the addition of an antibody, which proves the covalent binding of the antibody to the modified PMMA surface.

Figure 3C:
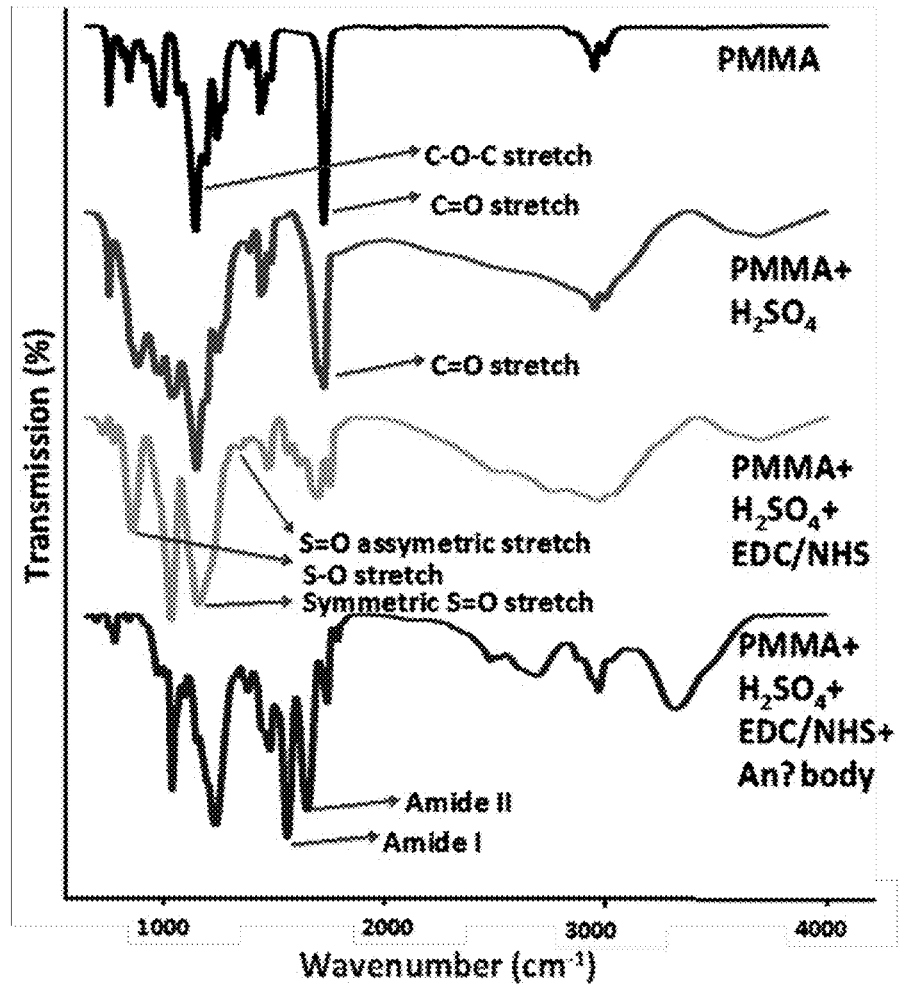

FT-IR of carboxylated PMMA (FIG. 3C). From FT-IR spectrum of the PMMA, it can be seen that there is a distinct absorption band from 1,150 $cm^{-1}$ to 1,250 $cm^{-1}$, which can be attributed to the C—O—C stretching vibration. The two bands at 1,387 $cm^{-1}$ and 750 $cm^{-1}$ can be attributed to the α-methyl group vibrations. The band at 986 $cm^{-1}$ is the characteristic absorption vibration of PMMA, together with the bands at 1,063 $cm^{-1}$ and 841 $cm^{-1}$. The band at 1,723 $cm^{-1}$ shows the presence of the acrylate carboxyl group. The band at 1,435 $cm^{-1}$ can be attributed to the bending vibration of the C—H bonds of the —$CH_3$ group. The two bands at 2,995 $cm^{-1}$ and 2,951 $cm^{-1}$ can be assigned to the C—H bond stretching vibrations of the —$CH_3$ and —$CH_2$— groups, respectively.

Some major changes can be observed in the spectrum of PMMA once it was modified. Treatment of PMMA with $H_2SO_4$ creates a carboxyl functional group in the PMMA surface. The splitted C=O stretch vibration for the acrylated (1724 $cm^{-1}$) and non-acrylated (1699 $cm^{-1}$) carboxyl group proves the formation of carboxyl functional group at the surface of PMMA. Then, the well-known EDC/NHS method was used to treat the carboxylated PMMA to get the amine-reactive sulfo-NHS ester, which can be proved by the S=O (1347 $cm^{-1}$) assymetric stretch, S—O (853 $cm^{-1}$) stretch and S=O (1152 $cm^{-1}$) symmetric stretch. A strong absorption for Amide I (1558 $cm^{-1}$) and Amide II (1646 $cm^{-1}$) can be seen after the addition of the antibody, which proves the covalent binding of the antibody to the modified PMMA surface.

Figure 4A:
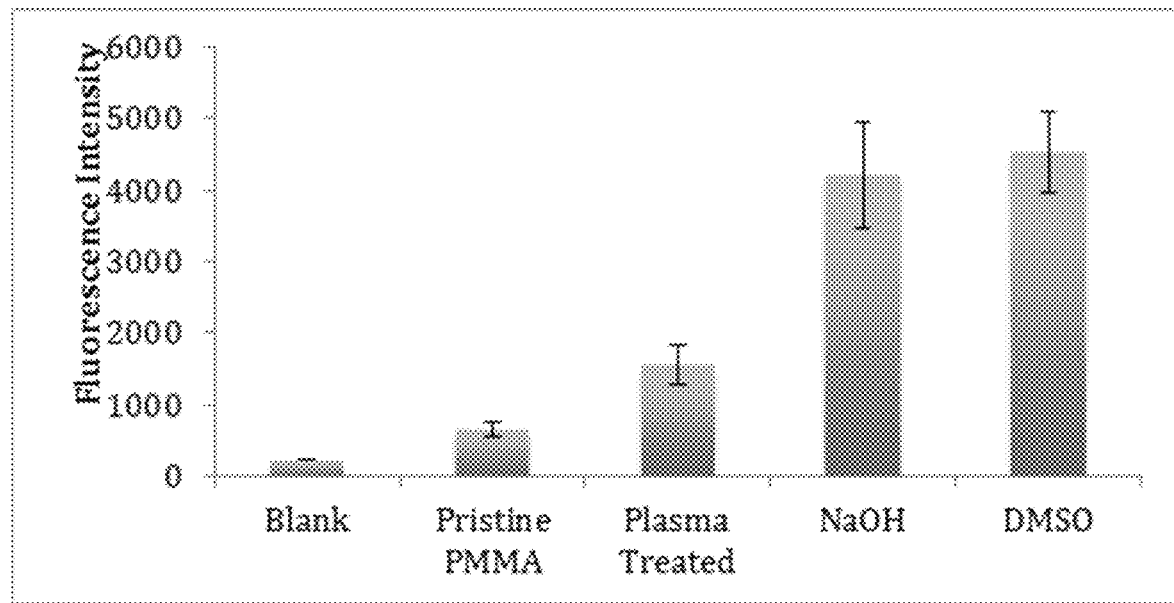
FIG. 4A-4B. Fluorescence intensity of surface modified PMMA. A. poly-lysine modification; B. Carboxylation.
Figure 4B:
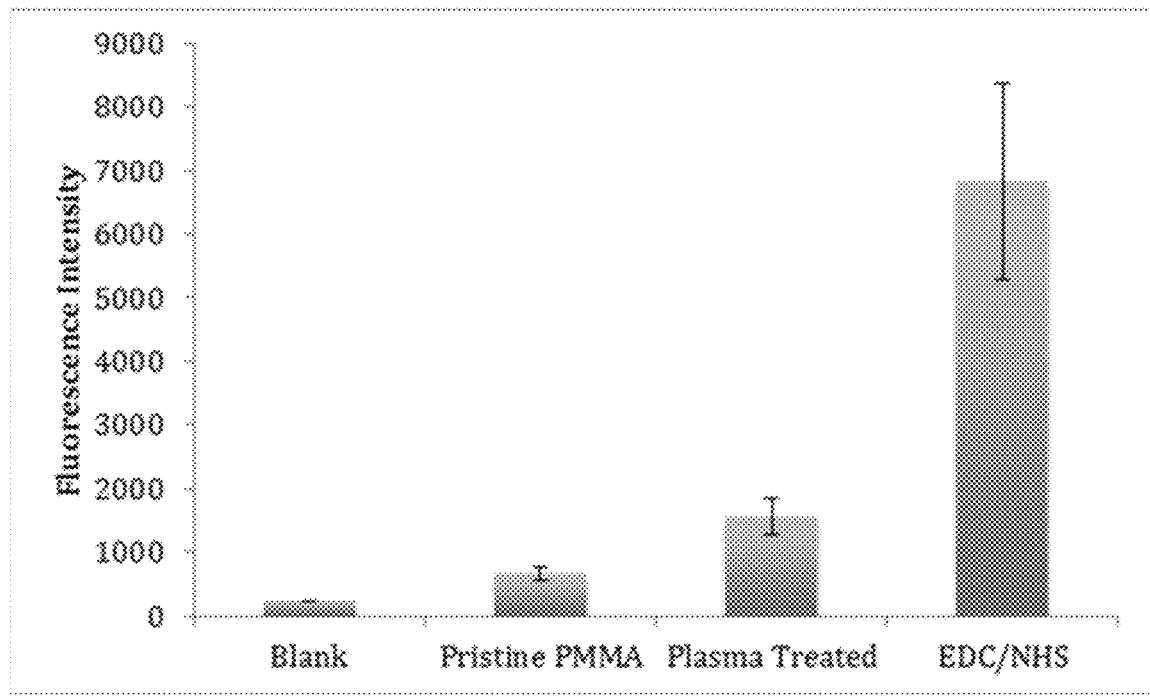

Once the PMMA was modified, 20 µg/mL of Cy-3 IgG was added to the PMMA surface and incubated for 20 minutes and washed with PBST for three times. Fluorescence intensity was measured before and after washing with PBST (FIG. 4A-4B). The covalent modification method with highest antibody binding will be used in subsequent experiment for multiplex infectious diseases detection.

Detection of IgG. For IgG detection assay, the primary Antibody, IgG (0.1 ng/mL-100 µg/mL in 10 mM, pH 8.0 PBS) was pipetted to the chip. After the chip was incubated with primary antibody for 20 minutes, the unreacted PMMA surface was blocked with Bovine Serum Albumin (4.5% BSA w/v in PBS+0.05% Tween 20) for another 20 minutes. After that, it was washed with washing buffer, PBST (10 mM, pH 7.4 PBS+0.05% Tween 20). Following washing, anti-rabbit IgG-Alkaline phosphatase (6 µg/mL) was added. It was then incubated for another 7 minutes. Then, the final wash was done with washing buffer for three times. Finally, the substrate for the alkaline phosphatase, i.e., BCIP/NBT (Nitroblue tetrazolium+5-bromo, 4-chloro, 3-indoyl phosphate) was added. NBT is used with the alkaline phosphatase substrate BCIP in western blotting and immunohistological staining and immunoassay procedures. These substrate systems produce an insoluble NBT diformazan end product that is blue to purple in color and can be observed visually. After 10 minutes, the PMMA was scanned with scanner and the brightness value was measured by using the software ImageJ.

Figures 5A, 5B:
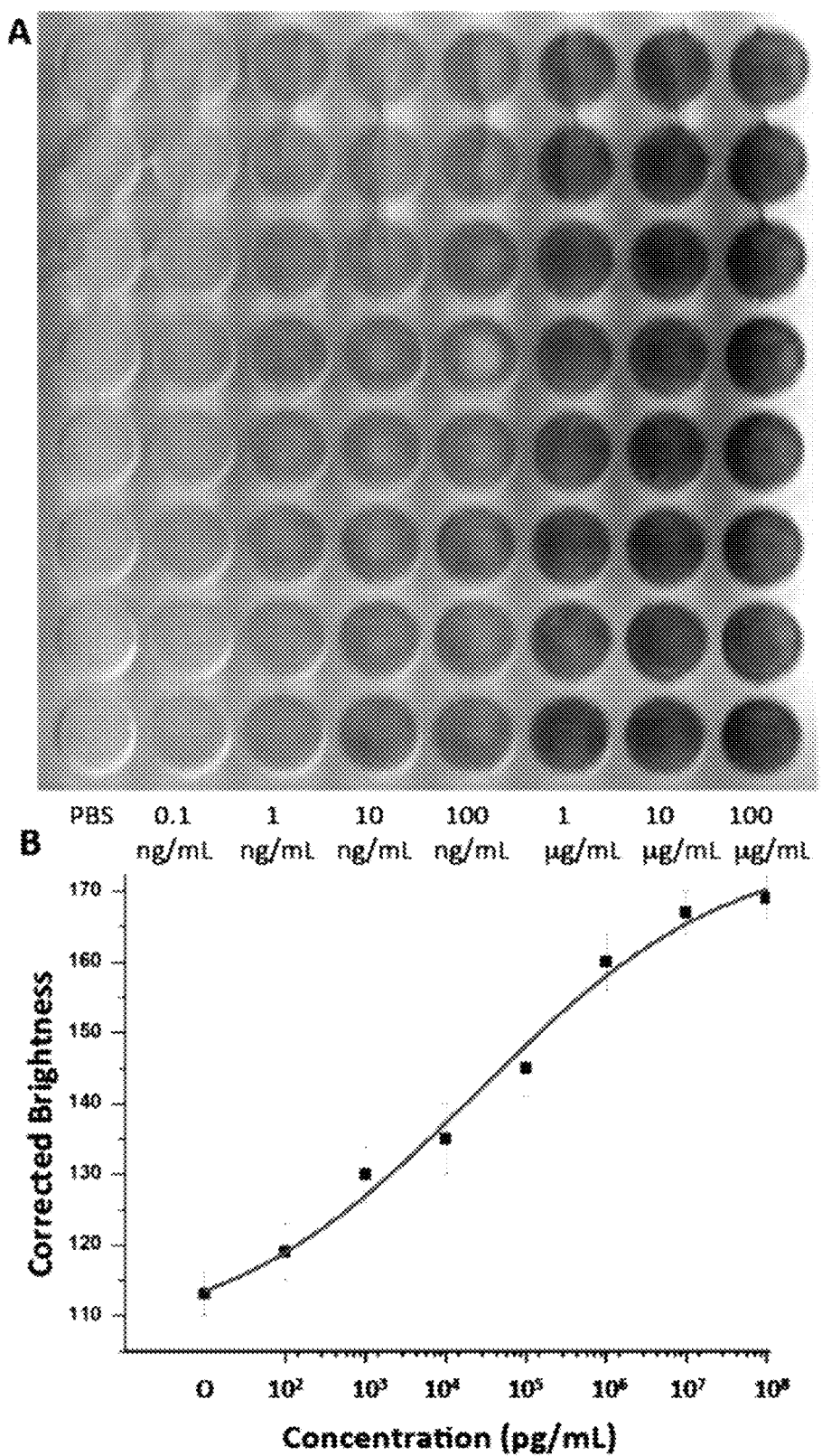
FIG. 5A-5B. Detection of IgG on poly-lysine modified PMMA (#1 method). (A) Scanned image of enzymatic converted substrate in different columns of the chip with concentrations from left to right: blank, 0.1 ng/mL, 1 ng/mL, 10 ng/mL, 100 ng/mL, 1 µg/mL, 10 µg/mL, and 100 µg/mL, respectively. (B) Sigmoidal curve of the corrected brightness of IgG over a concentration range of $10^2$ pg/mL to $10^8$ pg/mL.

The limit of detection (LOD) is defined as the concentration value that generates a signal three standard deviation above the blank value. The calibration curve of IgG on surface modified PMMA (#1 method) was linear over the range of $10^2$ pg/mL to $10^6$ pg/mL with a regression curve of y=9.72 log (x)+98.95 ($r^2$=0.98). The LOD of IgG on surface modified PMMA (#1 method) was found to be 200 pg/mL. (FIG. 5A-5B)

Figures 6A, 6B:
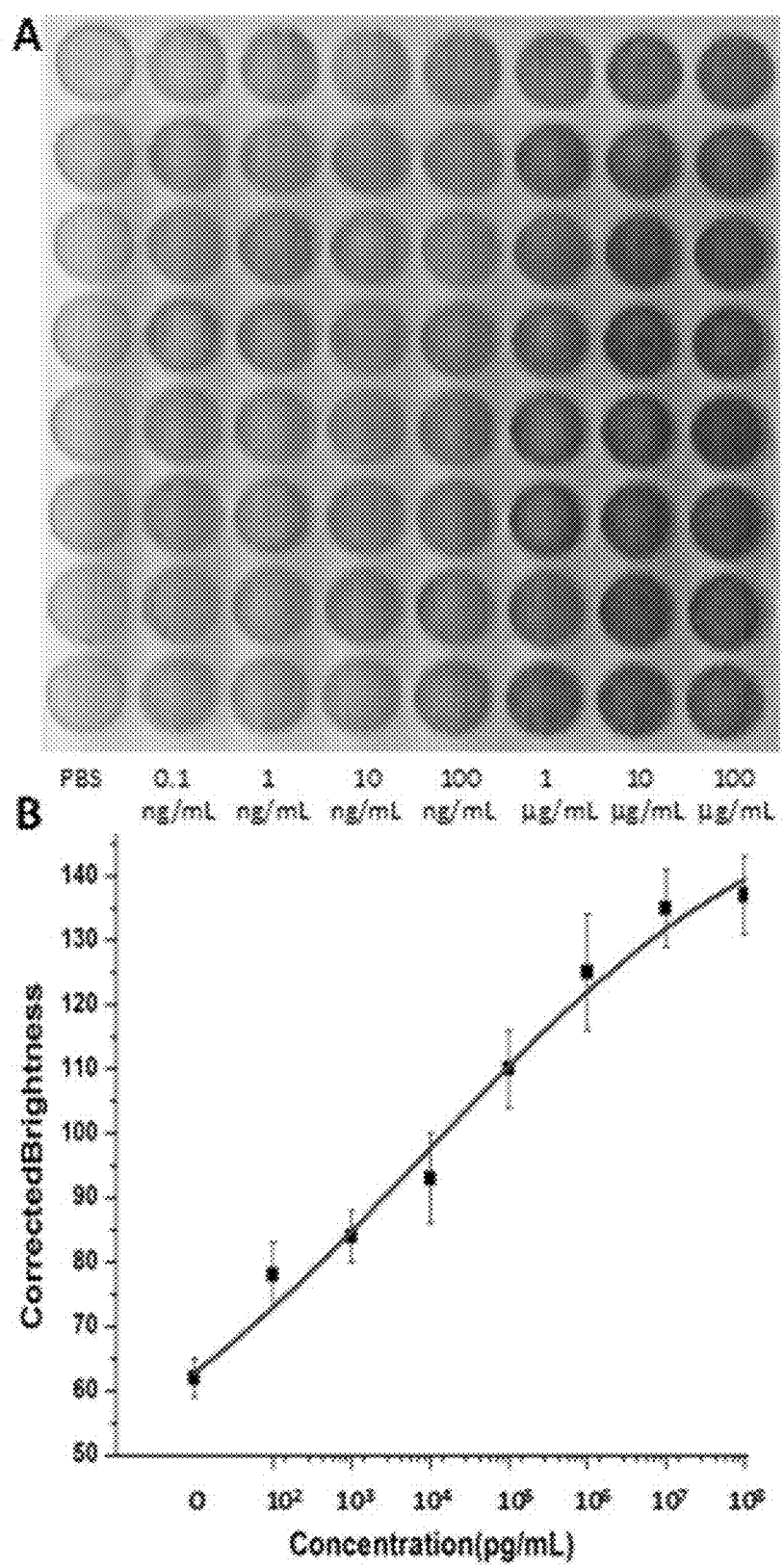
FIG. 6A-6B. Detection of IgG on poly-lysine modified PMMA (#2 method). (A) Scanned image of enzymatic converted substrate in different columns of the chip with concentrations from left to right: blank, 0.1 ng/mL, 1 ng/mL, 10 ng/mL, 100 ng/mL, 1 µg/mL, 10 µg/mL, and 100 µg/mL, respectively. (B) Sigmoidal curve of the corrected brightness of IgG over a concentration range of $10^2$ pg/mL to $10^8$ pg/mL.

The calibration curve of IgG on surface modified PMMA (#2 method) was linear over the range of $10^2$ pg/mL to $10^7$ pg/mL with a regression curve of y=12.26 log (x)+42.49 ($r^2$=0.98). The LOD of IgG on surface modified PMMA (#2 method) was found to be 140 pg/mL. (FIG. 6A-6B)

Figures 10A, 10B:
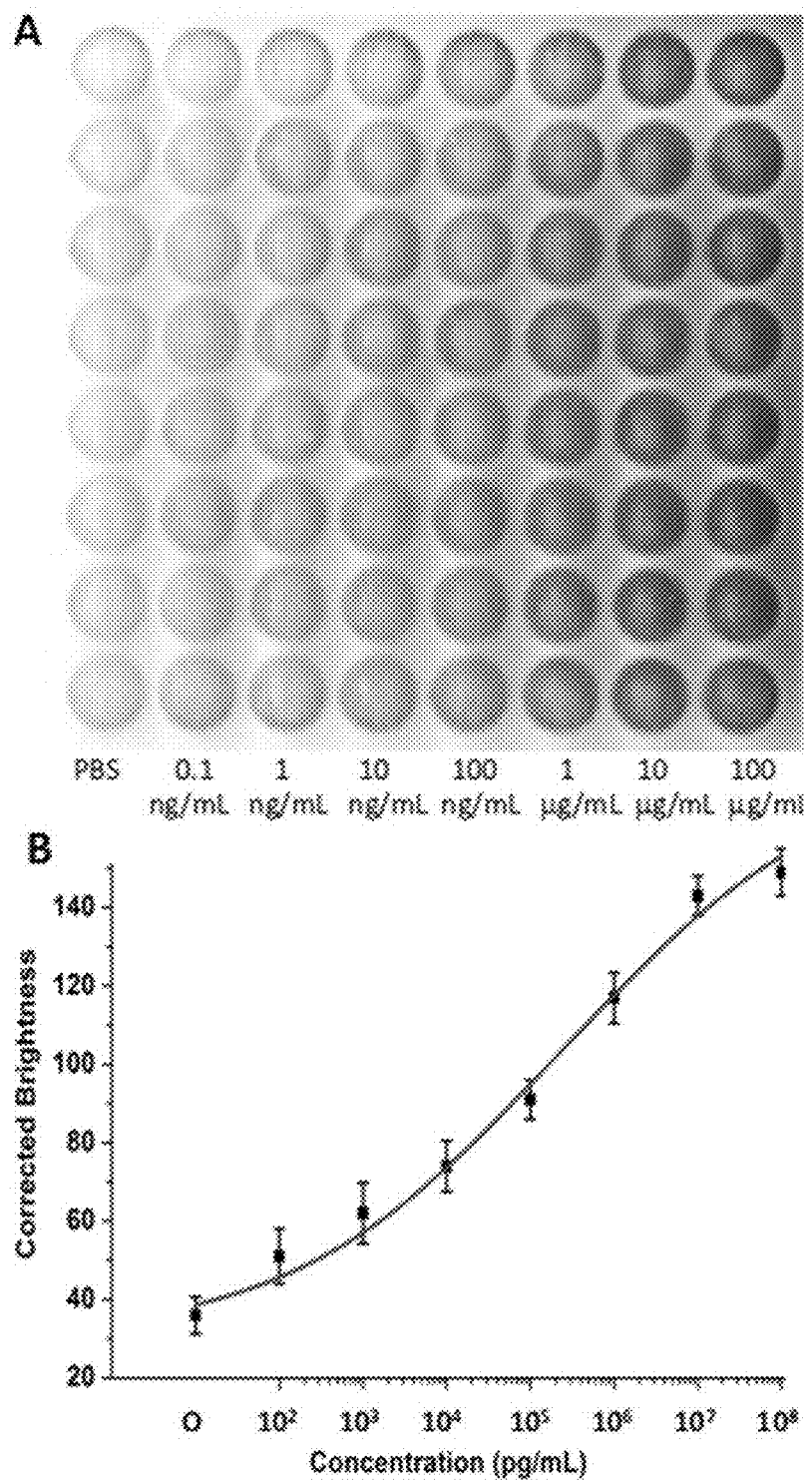
FIG. 10A-10B. Detection of IgG on surface modified PMMA (carboxylation). (A) Scanned image of enzymatic converted substrate in different columns of the chip with concentrations from left to right: blank, 0.1 ng/mL, 1 ng/mL, 10 ng/mL, 100 ng/mL, 1 µg/mL, 10 µg/mL, and 100 µg/mL, respectively. (B) Sigmoidal curve of the corrected brightness of IgG over a concentration range of $10^2$ pg/mL to $10^8$ pg/mL.

The limit of detection (LOD) is defined as the concentration value that generates a signal three standard deviation above the blank value. The calibration curve of IgG on surface modified PMMA was linear over the range of $10^2$ pg/mL to $10^8$ pg/mL with a regression curve of y=17.86 log (x)+9.57 ($r^2$=0.98). The LOD of IgG on surface modified PMMA was found to be 190 pg/mL. (FIG. 10A-10B)

HBsAg Detection assay. Different concentration of HBsAg (0.34 ng/mL-340 µg/mL in 10 mM, pH 8.0 PBS) was introduced to the wells in the modified PMMA surface. After the PMMA was incubated with antigen for 20 minutes, the unreacted PMMA surface was blocked with Bovine Serum Albumin (4.5% BSA w/v in PBS+0.05% Tween 20) for another 20 minutes. After that, primary antibody i.e., anti-HBsAg was added and incubated for 20 minutes. It was washed once with washing buffer, PBST (10 mM, pH 7.4 PBS+0.05% Tween 20). Following washing, alkaline phosphatase labelled secondary antibody (6 µg/mL) was added. It was again incubated for another 7 minutes. Then, the final wash was done with washing buffer for three times. Finally, the substrate for the alkaline phosphatase, i.e., BCIP/NBT (Nitroblue tetrazolium+5-bromo, 4-chloro, 3-indoyl phosphate) was added. After 10 minutes, the PMMA was scanned with scanner and the brightness value was measured using the software ImageJ.

Figures 7A, 7B:
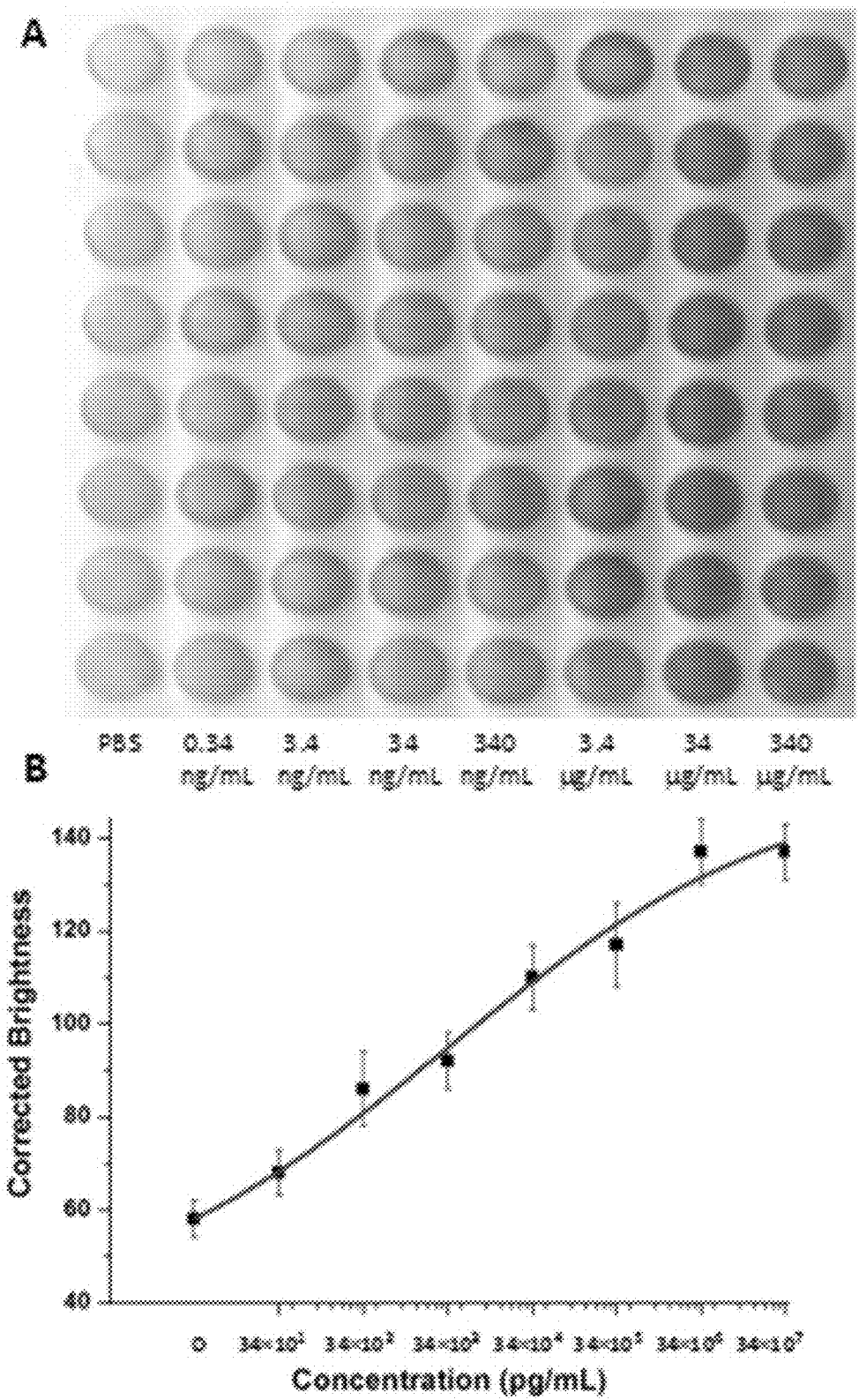
FIG. 7A-7B. Detection of HBsAg on poly-lysine modified PMMA (#1 method). (A) Scanned image of enzymatic converted substrate in different columns of the chip with concentrations, from left to right: blank, 0.34 ng/mL, 3.4 ng/mL, 34 ng/mL, 340 ng/mL, 3.4 µg/mL, 34 µg/mL, and 340 µg/mL, respectively. (B) Sigmoidal curve of the corrected brightness of ELISA of HBsAg over a concentration range of $34 \times 10^1$ pg/mL to $34 \times 10^7$ pg/mL.

The calibration curve of HBsAg on poly-lysine modified PMMA (#1 method) was linear over the range of 34×$10^1$ pg/mL to 34×$10^6$ pg/mL with a regression curve of y=13.13 log (x)+75.1 ($r^2$=0.98). The LOD of HBsAg on surface modified PMMA (#1 method) was found to be 180 pg/mL. (FIG. 7A-7B)

Figures 8A, 8B:
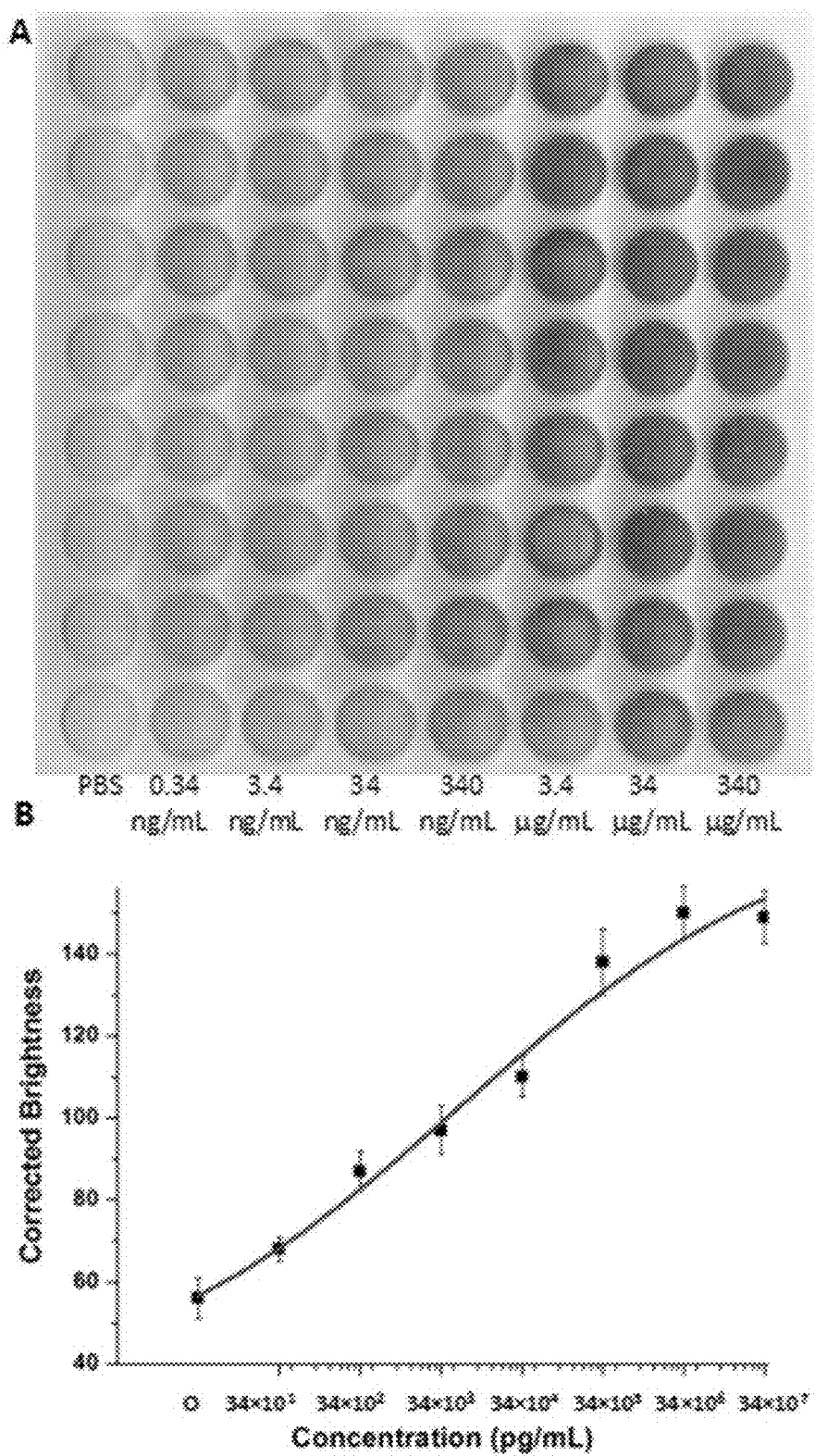
FIG. 8A-8B. Detection of HBsAg on poly-lysine modified PMMA (#2 method). (A) Scanned image of enzymatic converted substrate in different columns of the chip with concentrations, from left to right: blank, 0.34 ng/mL, 3.4 ng/mL, 34 ng/mL, 340 ng/mL, 3.4 µg/mL, 34 µg/mL, and 340 µg/mL, respectively. (B) Sigmoidal curve of the corrected brightness of ELISA of HBsAg over a concentration range of $34 \times 10^1$ pg/mL to $34 \times 10^7$ pg/mL.
Figures 9A, 9B:
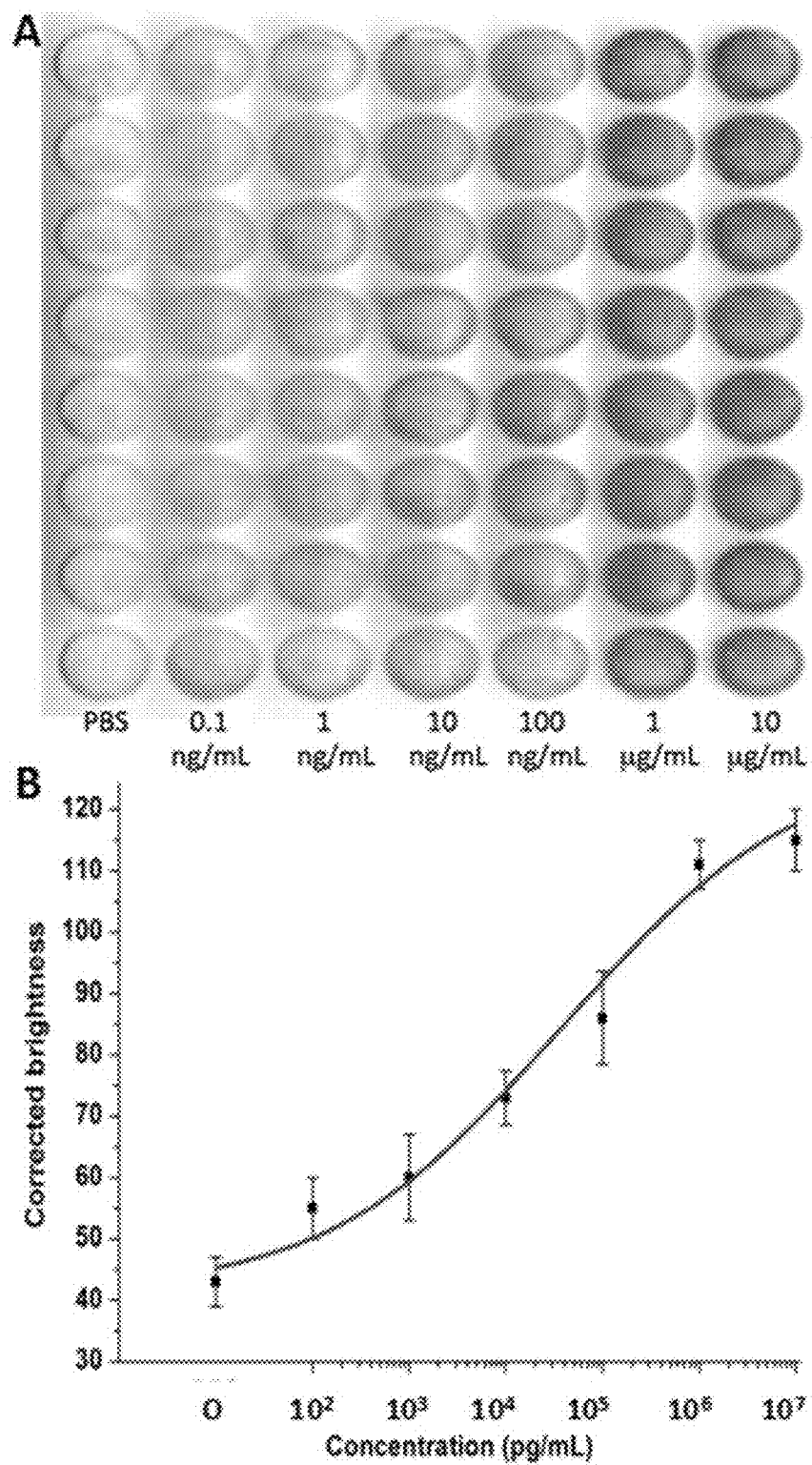
FIG. 9A-9B. Detection of HBcAg on surface modified PMMA (poly-lysine). (A) Scanned image of enzymatic converted substrate in different columns of the chip with concentrations from left to right: blank, 0.1 ng/mL, 1 ng/mL, 10 ng/mL, 100 ng/mL, 1 µg/mL, and 10 µg/mL, respectively. (B) Sigmoidal curve of the corrected brightness of HBcAg over a concentration range of $10^2$ pg/mL to $10^7$ pg/mL.

The calibration curve of HBsAg on poly-lysine modified PMMA (#2 method) was linear over the range of 34×$10^1$ pg/mL to 34×$10^6$ pg/mL with a regression curve of y=16.46 log (x)+74.9 ($r^2$=0.98). The LOD of HBsAg on surface modified PMMA (#2 method) was found to be 160 pg/mL. (FIG. 8A-8B)

Figures 11A, 11B:
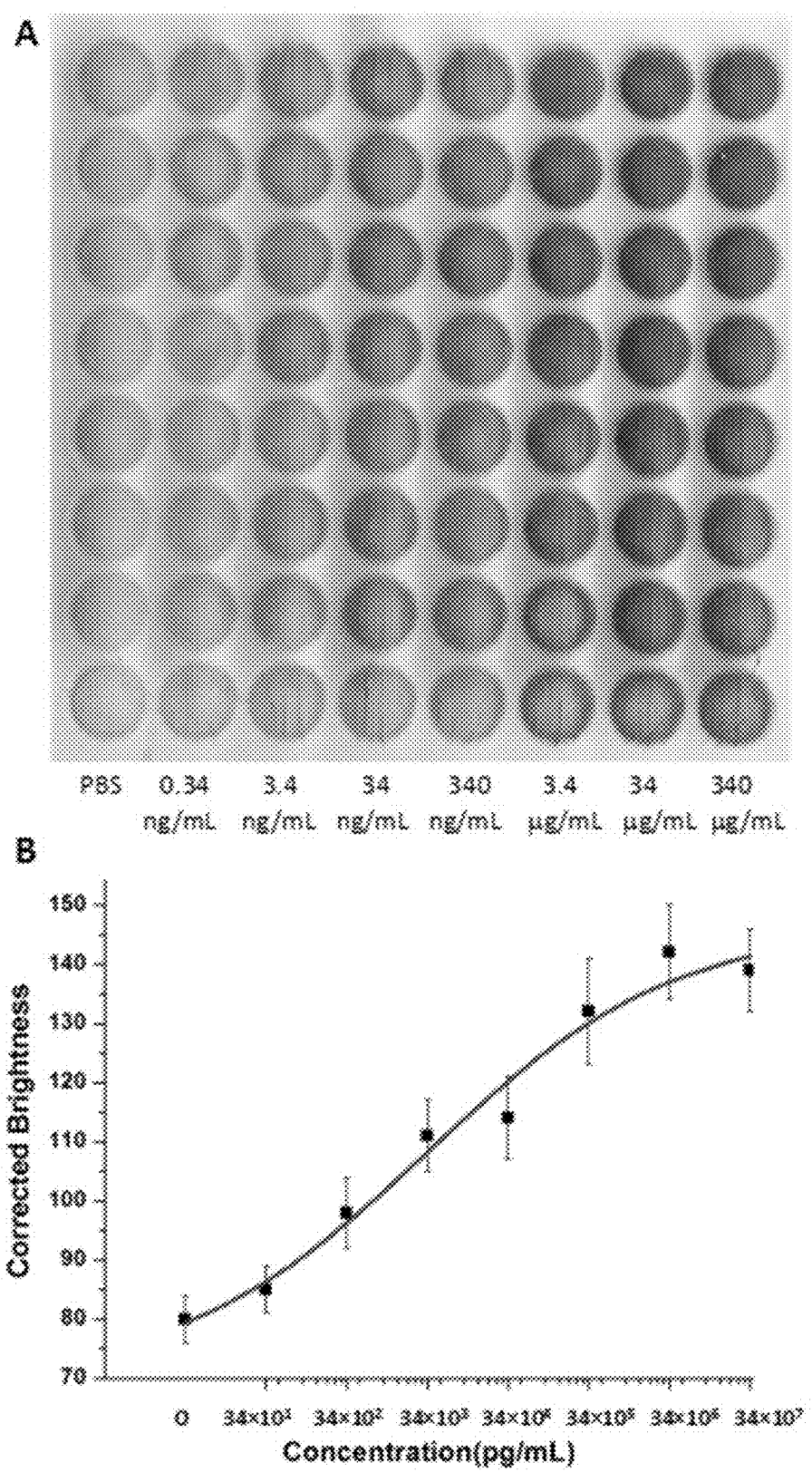
FIG. 11A-11B. Detection of HBsAg on surface modified PMMA (carboxylation). (A) Scanned image of enzymatic converted substrate in different columns of the chip with concentrations, from left to right: blank, 0.34 ng/mL, 3.4 ng/mL, 34 ng/mL, 340 ng/mL, 3.4 µg/mL, 34 µg/mL, and 340 µg/mL, respectively. (B) Sigmoidal curve of the corrected brightness of ELISA of HBsAg over a concentration range of $34 \times 10^1$ pg/mL to $34 \times 10^7$ pg/mL.

The calibration curve of HBsAg on carboxylated PMMA was linear over the range of 34×$10^1$ pg/mL to 34×$10^6$ pg/mL with a regression curve of y=11.05 log (x)+91.76 ($r^2$=0.98). The LOD of HBsAg on surface modified PMMA was found to be 360 pg/mL. (FIG. 11A-11B)

Detection of HBcAg. Different concentration of HBcAg (0.1 ng/mL-10 µg/mL in 10 mM, pH 8.0 PBS) was introduced to the wells in the modified PMMA surface. After the PMMA was incubated with Antigen for 20 minutes, the unreacted PMMA surface was blocked with Bovine Serum Albumin (4.5% BSA w/v in PBS+0.05% Tween 20) for another 20 minutes. After that, primary antibody i.e., anti-HBsAg was added and incubated for 20 minutes. It was washed once with washing buffer, PBST (10 mM, pH 7.4 PBS+0.05% Tween 20). Following washing, alkaline phosphatase labelled secondary antibody (6 µg/mL) was added. It was again incubated for another 7 minutes. Then, the final wash was done with washing buffer for three times. Finally, the substrate for the alkaline phosphatase, i.e., BCIP/NBT (Nitroblue tetrazolium+5-bromo, 4-chloro, 3-indoyl phosphate) was added. After 10 minutes, the PMMA was scanned with scanner and the brightness value was measured using the software ImageJ.

Figures 12A, 12B:
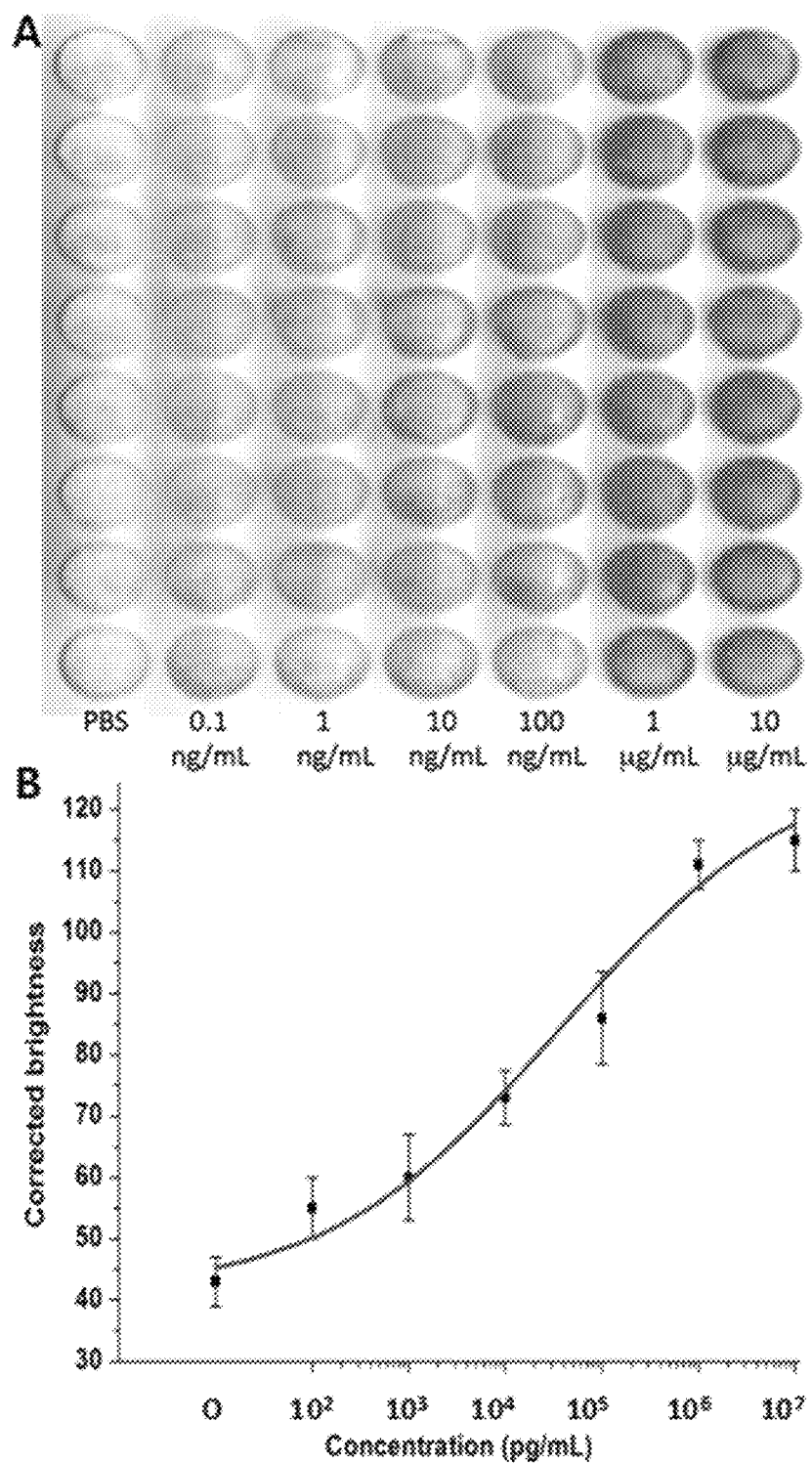
FIG. 12A-12B. Detection of HBcAg on surface modified PMMA (carboxylation). (A) Scanned image of enzymatic converted substrate in different columns of the chip with concentrations from left to right: blank, 0.1 ng/mL, 1 ng/mL, 10 ng/mL, 100 ng/mL, 1 µg/mL, and 10 µg/mL, respectively. (B) Sigmoidal curve of the corrected brightness of HBcAg over a concentration range of $10^2$ pg/mL to $10^7$ pg/mL.
Figures 13A, 13B:
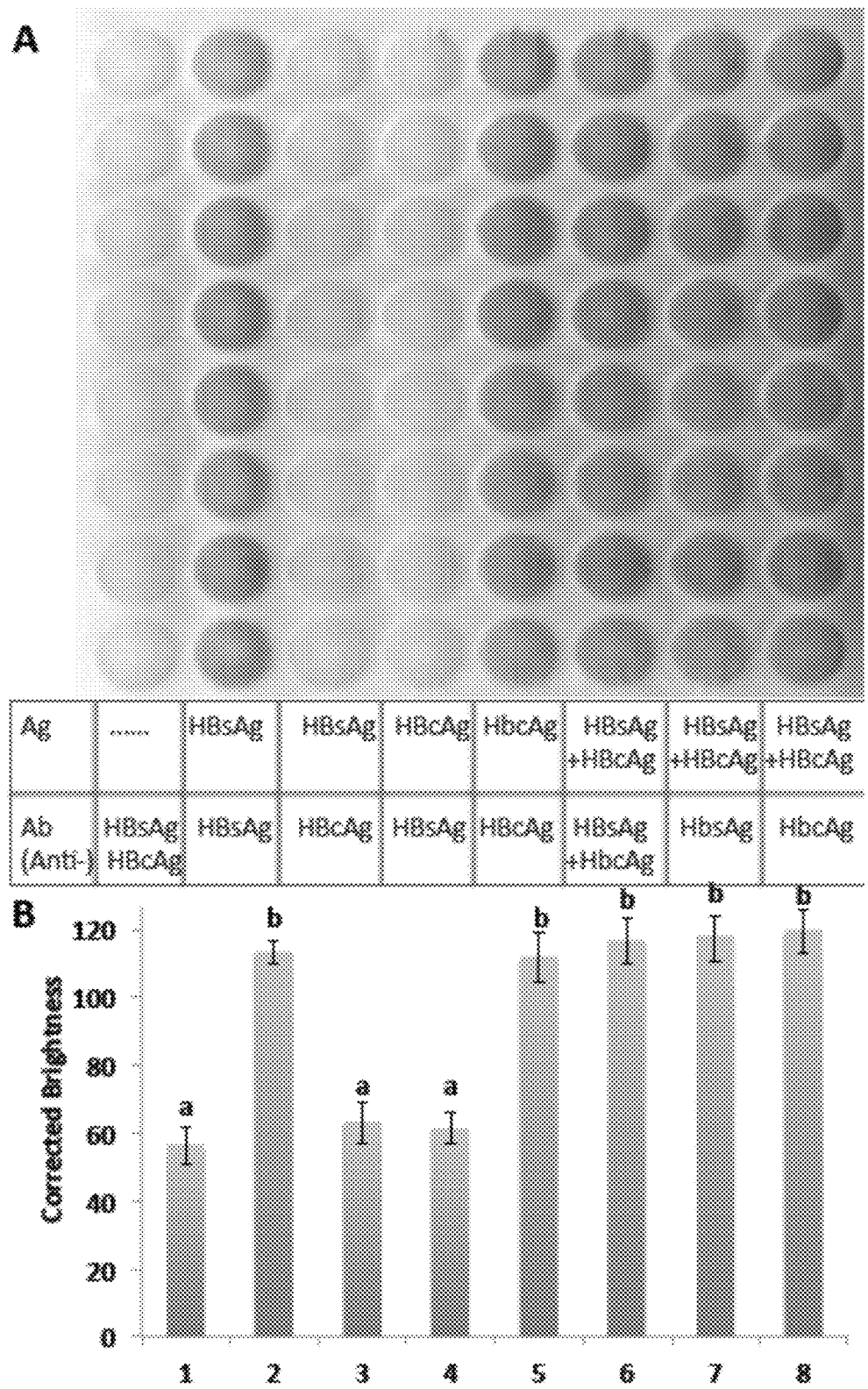
FIG. 13A-13B. Multiplex assay in surface modified PMMA (poly-lysine). Scanned image of the enzyme-catalyzed substrate, (A) and bar plot of corrected brightness of the scanned image (B) for detection of HBsAg and HBcAg. From left to right: immobilized probe, none (1), HBsAg (2) and (3), HBcAg (4) and (5), and HBsAg+HBcAg (6), (7), and (8), respectively. Test: From left to right, solution containing, anti-HBsAg and anti-HBcAg (1) and (6), HBsAg (2), (4), and (7), and HBcAg (3), (5), and (8). "a" and "b" shows that the data are significantly different from each other at p=0.05.
Figures 14A, 14B:
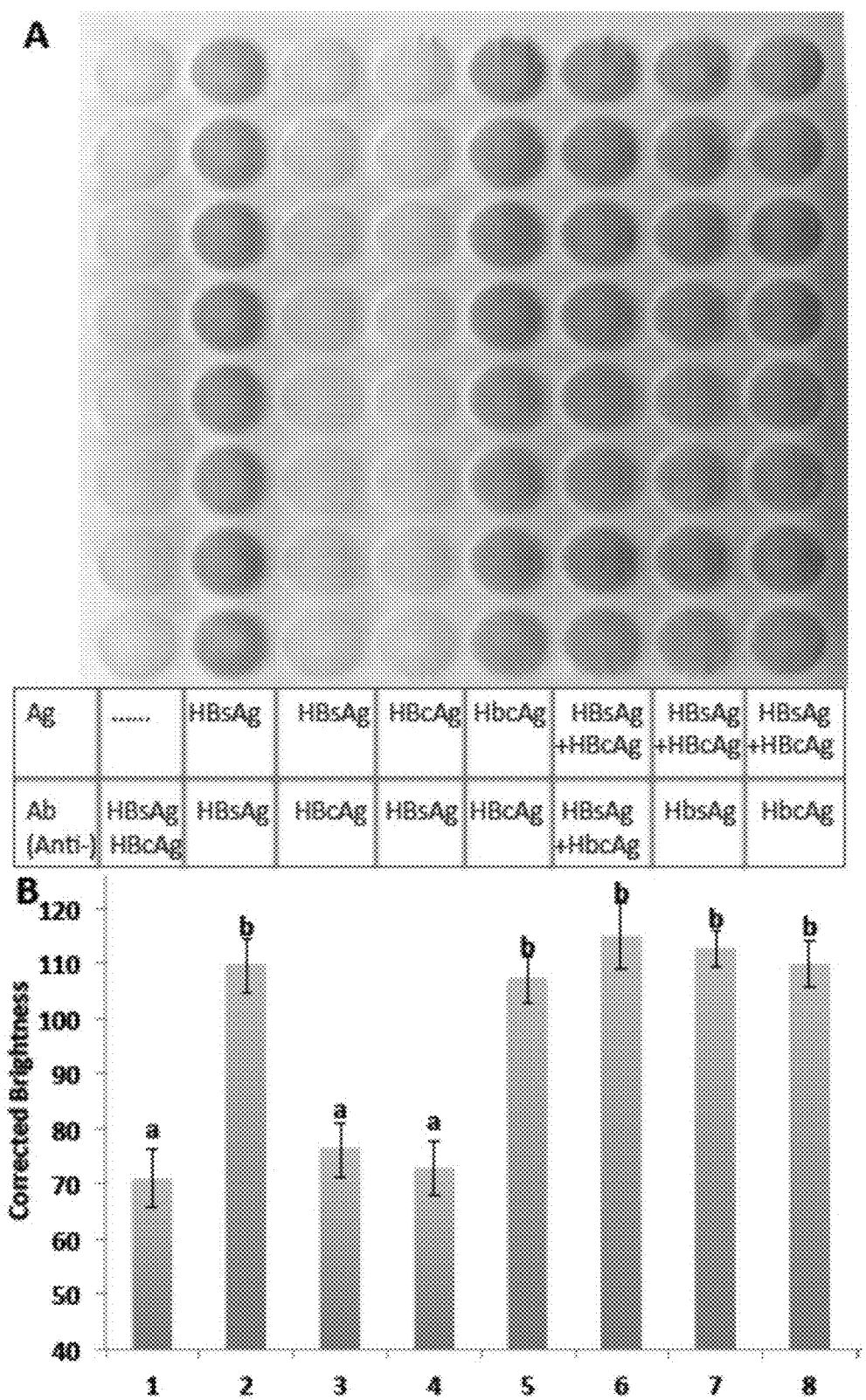
FIG. 14A-14B. Multiplex assay in surface modified PMMA (carboxylation). Scanned image of the enzyme-catalyzed substrate, (A) and bar plot of corrected brightness of the scanned image (B) for detection of HBsAg and HBcAg. From left to right: immobilized probe, none (1), HBsAg (2) and (3), HBcAg (4) and (5), and HBsAg+HBcAg (6), (7), and (8), respectively. Test: From left to right, solution containing, anti-HBsAg and anti-HBcAg (1) and (6), HBsAg (2), (4), and (7), and HBcAg (3), (5), and (8). "a" and "b" shows that the data are significantly different from each other at p=0.05.
Figures 15A, 15B:
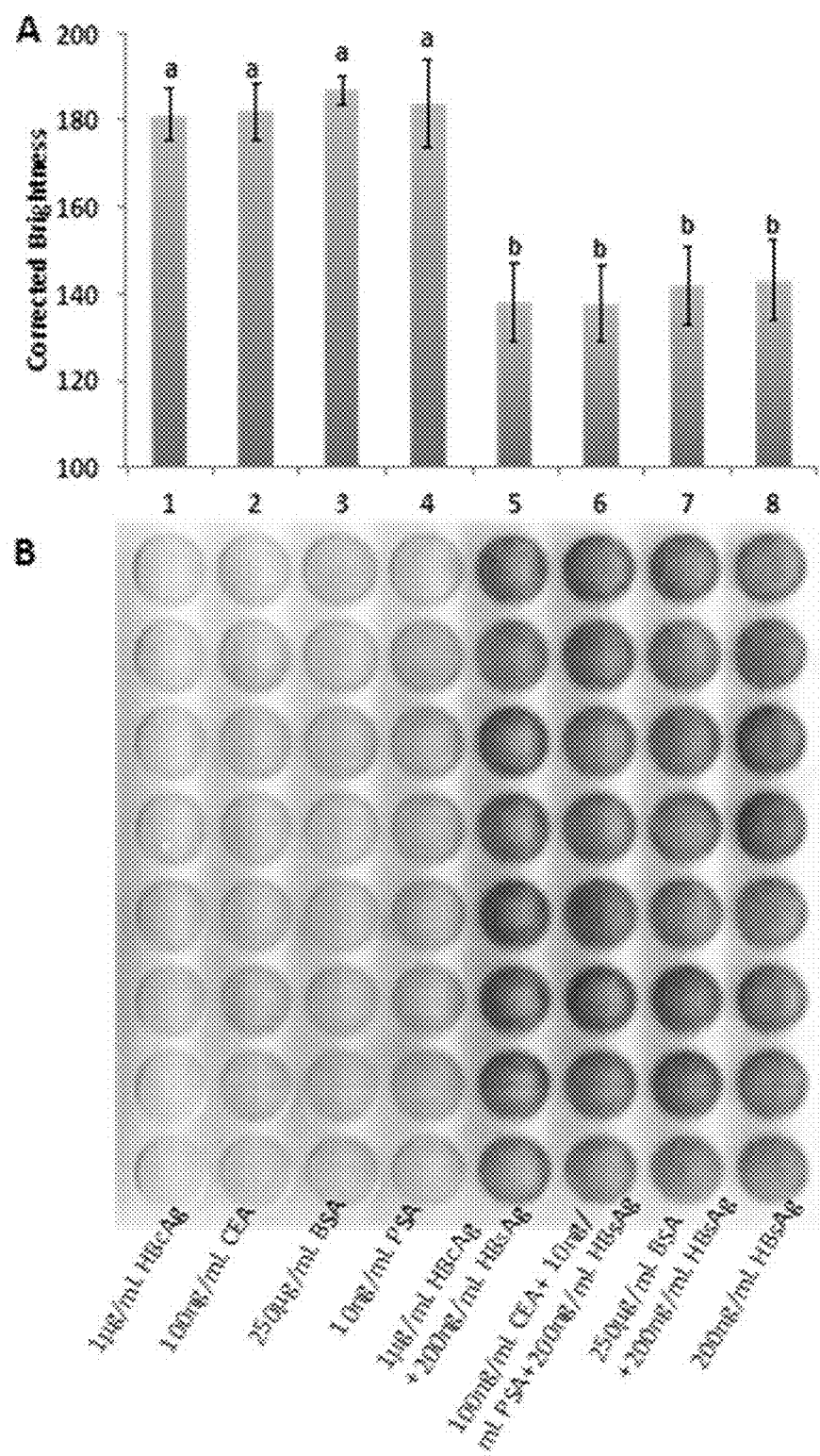
FIG. 15A-15B. Anti-interference test for the detection of HBsAg in surface modified PMMA (poly-lysine). Corrected brightness of the scanned image of ELISA as measured by ImageJ (A) and scanned image of the chip (B) for the detection of HBsAg. From left to right: detection of 0 ng/mL of HBsAg in the solution containing 1 µg/mL HBcAg (1), 100 ng/mL CEA (2), 250 µg/mL BSA (3), and 10 ng/mL PSA (4), respectively and 200 ng/mL of HBsAg in 1 µg/mL HBcAg (5), 100 ng/mL CEA+10 ng/mL PSA (6), 250 µg/mL BSA (7), and PBS (8), respectively. "a" and "b" shows that the data are significantly different from each other at p=0.05.
Figures 16A, 16B:
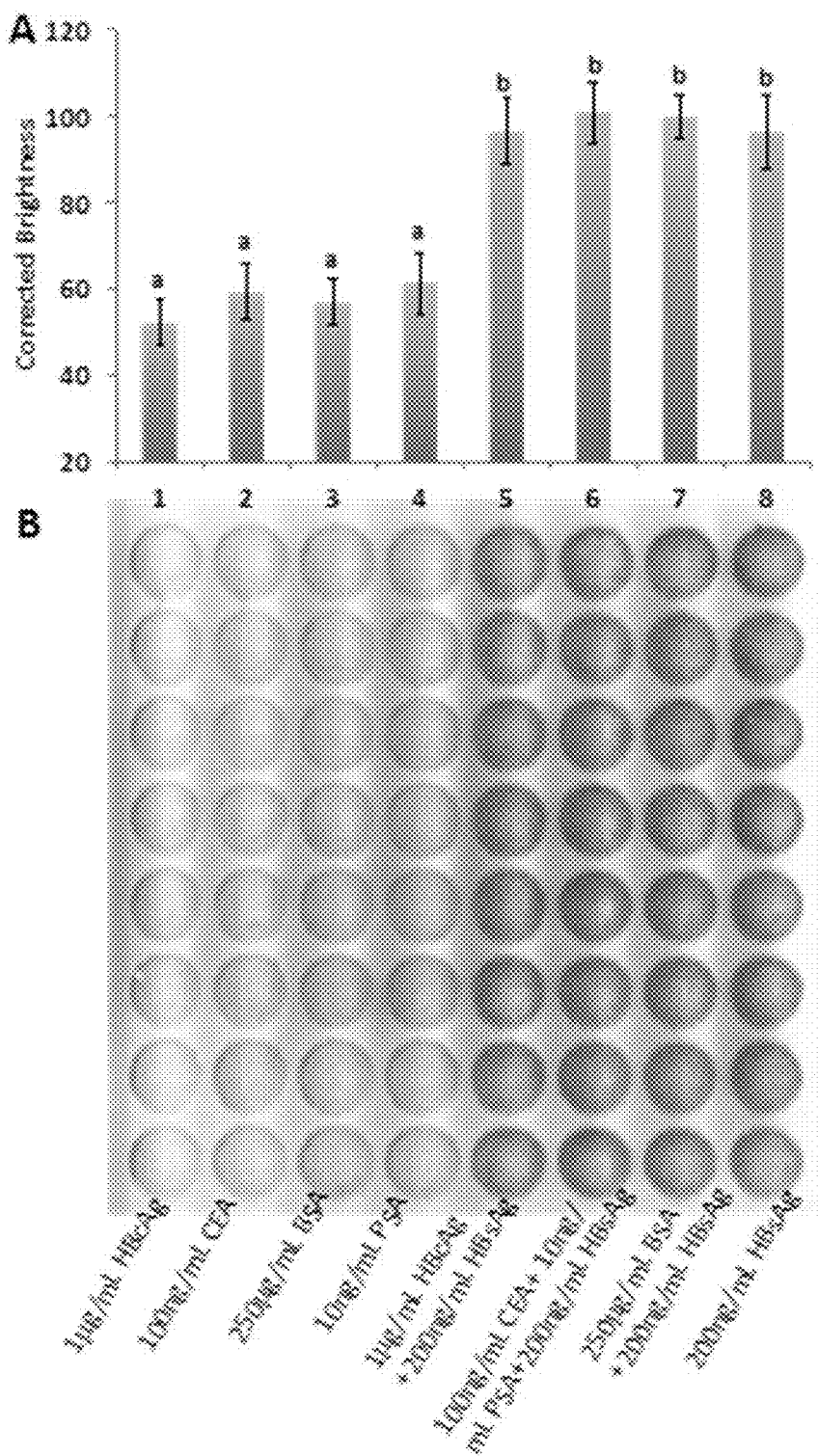
FIG. 16A-16B. Anti-interference test for the detection of HBsAg in surface modified PMMA (carboxylation). Corrected brightness of the scanned image of ELISA as measured by ImageJ (A) and scanned image of the chip (B) for the detection of HBsAg. From left to right: detection of 0 ng/mL of HBsAg in the solution containing 1 µg/mL HBcAg (1), 100 ng/mL CEA (2), 250 µg/mL BSA (3), and 10 ng/mL PSA (4), respectively and 200 ng/mL of HBsAg in 1 µg/mL HBcAg (5), 100 ng/mL CEA+10 ng/mL PSA (6), 250 µg/mL BSA (7), and PBS (8), respectively. "a" and "b" shows that the data are significantly different from each other at p=0.05.

The calibration curve of HBcAg on surface modified PMMA was linear over the range of $10^2$ pg/mL to $10^7$ pg/mL with a regression curve of y=14.07 log (x)+29.64 ($r^2$=0.98). The LOD of HBcAg on surface modified PMMA was found to be 380 pg/mL. (FIG. 12A-12B)

Multiplex Detection. The surface modified PMMA was used for simultaneous colorimetric detection of HBsAg and HBcAg. As shown in the diagram first column is negative control without any antigen, hence no color development. Second and third columns are for the detection of HBsAg while fourth and fifth columns are for the detection of HBcAg. Third and fourth columns do not develop color, as they do not have the respective antibody against the antigen but second and fifth columns develop color as they have their respective antibody. Sixth, seventh and eight columns have both the antigen i.e. HBsAg and HBcAg. All of them develop color as they have their respective antibody or the mixture of both the antibody. (FIG. 13A-13B and FIG. 14A-14B)

Anti-interference Test. The detection assay needs to have a high anti-interference capability to screen various infectious diseases as the serum contains complex ingredients consisting of hundreds of different proteins with a wide range of concentration that may interfere the detection of target proteins. Anti-interference experiments were performed in the various columns of the modified PMMA. The experiment shows the detection of HBsAg 200 ng/mL with and without various interfering proteins (1 µg/mL HBcAg, 100 ng/mL carcinoembryonic antigen (CEA), 250 µg/mL BSA, and 10 ng/mL prostate specific antigen (PSA)). As shown in the diagram, first four columns do not contain HBsAg while the last four columns contains 200 ng/mL of HBsAg with various concentration of interfering proteins. In the absence of HBsAg, there is no development of color. Furthermore, the color intensity for the detection of 200 ng/mL of HBsAg in the presence of different interfering protein was similar to the detection of 200 ng/mL of HBsAg without the interfering protein. It demonstrates that even 1,250 times concentrated interfering proteins could not influence the specific detection of HBsAg. (FIG. 15A-15B and FIG. 16A-16B).

The invention claimed is:

1. An ultrasensitive microfluidic microtiter plate comprising a plurality of microwells having poly-lysine covalently coupled to a poly(methyl methacrylate) (PMMA) surface and further comprising a glutaraldehyde linker coupled to the poly-lysine and a capture protein or peptide, wherein the plate has a limit of detection for IgG of 200 pg/mL.

2. The microtiter plate of claim 1, wherein the capture protein is an antibody or antibody fragment.

3. The microtiter plate of claim 1, wherein the plate comprises 8 or more microwells.

4. The microtiter plate of claim 3, wherein the plate comprises 96 to 800 microwells.

5. The microtiter plate of claim 3, wherein each microwell is about 0.001 to 3 mm in diameter and 0.01 to 4 mm in depth.

6. The microtiter plate of claim 1, wherein the microwells have a flat or rounded floor.

7. The microtiter plate of claim 1, wherein the microwells are funnel shaped, having an upper diameter of 0.1 to 5 mm and a lower diameter of 0.001 to 1 mm.

8. The microtiter plate of claim 1, wherein the microwells are arranged in an array.

9. The microtiter plate of claim 8, wherein the array is a radial array or columnar array.

10. An enzyme linked immunosorbent assay (ELISA) kit comprising the microtiter plate of claim 1.

11. The kit of claim 10, further comprising a capture agent.

12. The kit of claim 11, wherein the kit comprises a plurality of capture agents.

13. The kit of claim 11, wherein the capture agent is coupled to the microtiter plate.

14. The kit of claim 11, wherein the capture agent is provided in a container separate from the microtiter plate.

15. The kit of claim 11, wherein the capture agent is an antibody.

16. The kit of claim 11, further comprising detection reagents and wash reagents.

17. A method for detecting an analyte in a sample comprising:
   contacting an microtiter plate of claim 1, comprising a capture agent covalently bound to the microtiter plate, wherein the capture agent binds a target analyte, with a sample suspected of comprising the target analyte; and detecting the presence of a signal.

18. The method of claim 17, wherein the signal is detected by direct visualization or by or an office scanner.

* * * * *